US008260010B2

(12) United States Patent
Chhibber et al.

(10) Patent No.: US 8,260,010 B2
(45) Date of Patent: *Sep. 4, 2012

(54) SYSTEMS AND METHODS FOR ANALYZING SKIN CONDITIONS OF PEOPLE USING DIGITAL IMAGES

(75) Inventors: Rajeshwar Chhibber, San Jose, CA (US); Ashutosh Chhibber, San Jose, CA (US); Shefali Sharma, Petaluma, CA (US)

(73) Assignee: BrighTex Bio-Photonics LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/352,324

(22) Filed: Jan. 12, 2009

(65) Prior Publication Data

US 2009/0141956 A1 Jun. 4, 2009

Related U.S. Application Data

(63) Continuation of application No. 11/476,278, filed on Jun. 27, 2006, now Pat. No. 7,477,767, which is a continuation-in-part of application No. 11/232,452, filed on Sep. 20, 2005, now Pat. No. 7,454,046.

(51) Int. Cl.
*G06K 9/00* (2006.01)
(52) U.S. Cl. ........ 382/118; 382/128; 382/224; 600/306; 600/473; 600/476
(58) Field of Classification Search .................. 382/118, 382/128, 224; 600/306, 407, 473, 476, 477, 600/478
See application file for complete search history.

(56) References Cited

U.S. PATENT DOCUMENTS

| | | | |
|---|---|---|---|
| 4,236,082 A | 11/1980 | Butler | |
| 4,894,547 A | 1/1990 | Leffell et al. | |
| 5,074,306 A | 12/1991 | Green et al. | |
| 5,343,536 A | 8/1994 | Groh | |
| 5,363,854 A | 11/1994 | Martens et al. | |
| 5,836,872 A | 11/1998 | Kenet et al. | |
| 6,571,003 B1 | 5/2003 | Hillebrand et al. | |
| 7,233,693 B2 | 6/2007 | Momma | |
| 7,349,857 B2 | 3/2008 | Manzo | |
| 7,454,046 B2 | 11/2008 | Chhibber et al. | |
| 7,477,767 B2 | 1/2009 | Chhibber et al. | |
| 2004/0125996 A1* | 7/2004 | Eddowes et al. | 382/128 |

(Continued)

OTHER PUBLICATIONS

Liangen, et al., "Human Skin Surface Evaluation by Image Processing," *Proceedings of SPIE, Third International Conference on Photonics and Imaging in Biology and Medicine*, 5254:362-367 (2003).

(Continued)

*Primary Examiner* — Gregory M Desire
(74) *Attorney, Agent, or Firm* — Morgan, Lewis & Bockius LLP; Richard F. Trecartin

(57) ABSTRACT

Systems and methods are provided for analyzing skin conditions using digital images. The method comprises acquiring a white-light image and an ultraviolet ("UV") image of at least a portion of a body surface, such as a person's face, each of the white-light and UV images including a plurality of pixels and each pixel in the UV image corresponding to a respective pixel in the white-light image. The method further comprises identifying skin-pixels in the white-light and UV images, and obtaining results associated with at least one skin condition using information in the skin pixels in the first white light and UV images.

27 Claims, 24 Drawing Sheets

U.S. PATENT DOCUMENTS

| | | | |
|---|---|---|---|
| 2008/0051773 A1* | 2/2008 | Ivanov et al. | 606/12 |
| 2008/0212894 A1* | 9/2008 | Demirli et al. | 382/276 |
| 2009/0196475 A1* | 8/2009 | Demirli et al. | 382/128 |

OTHER PUBLICATIONS

Sandby-Moller, "Influence of Epidermal Thickness, Pigmentation and Redness on Skin Autofluorescence [para]," *American Society of Photobiology*, pp. 1-9 (Jun. 2003).

Sboner, et al., "Clinical Validation of an Automated System for Supporting the Early Diagnosis of Melanoma," *Skin Research and Technology*, 10:184-192 (2004).

Zeng, et al., "Autofluorescence Properties of Skin and Application in Dermatology," *Proceedings of SPIE*, 4224:366-373 (2000).

Hsu, et al., "Face Detection in Color Images," *IEEE Transactions on Pattern Analysis and Machine Intelligence*, 24(5):696-706 (2002).

Kollias, et al., "Optical Non-Invasive Approaches to Diagnosis of Skin Diseases," *OCT JID Symposium Proceedings*, 7:64-75 (2002).

\* cited by examiner

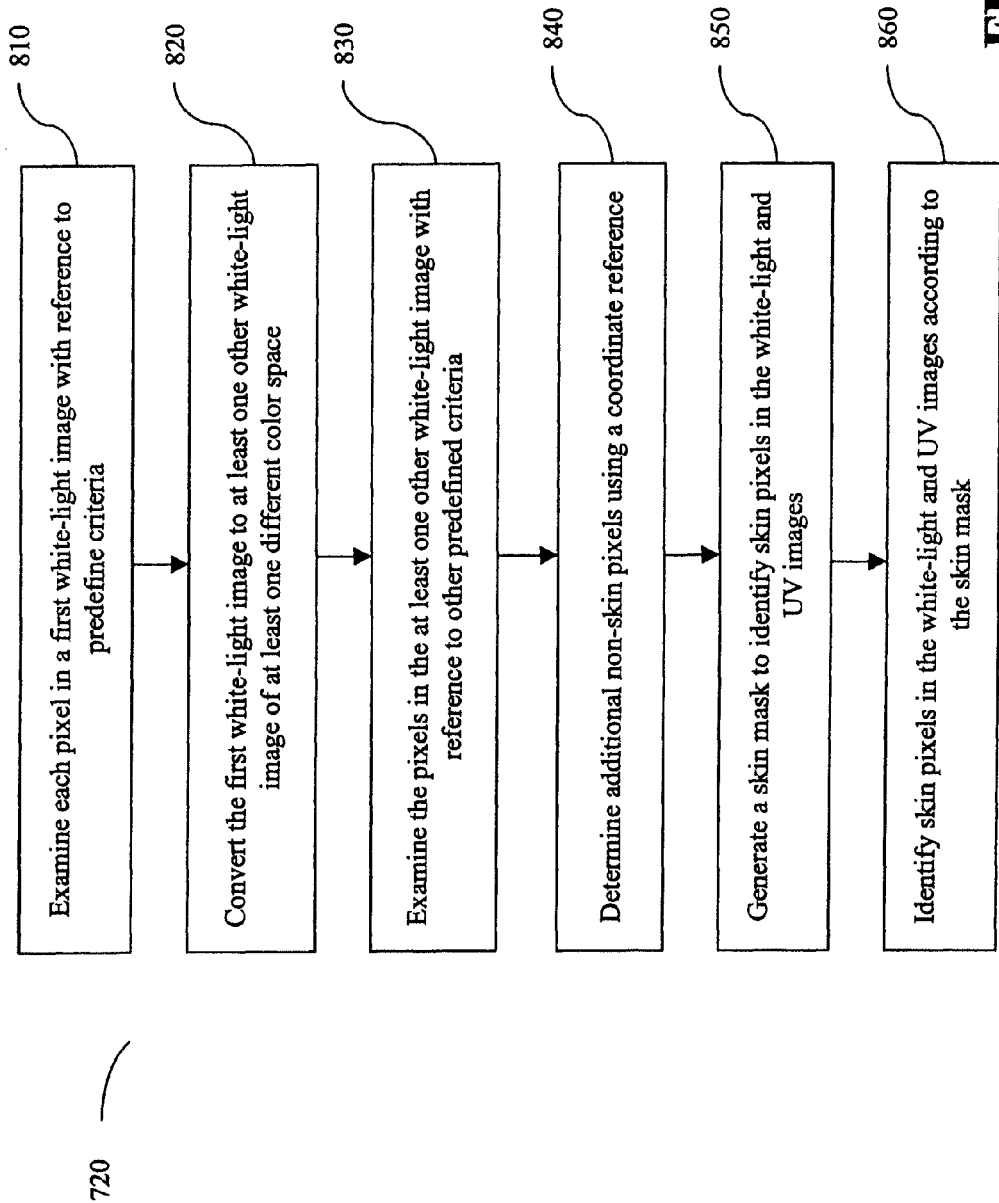

Range for each color channel
likely associated with skin pixel

| Color Space | Channel 1 | Channel 2 | Channel 3 |
|---|---|---|---|
| RGB | 105 – 255 | 52 – 191 | 32 – 180 |
| YIQ | 66 – 206 | 20 – 77 | 0 – 32 |
| LAB | 132 – 165 | 133 – 150 | 170 – 230 |
| YcBcR | 149 – 200 | 85 – 123 | 80 – 190 |
| HSV | 140 – 255 | 62 – 162 | 0 – 41 |

FIG. 9B

| Skin Condition | Color | Values |
|---|---|---|
| Inflamed Pores | White | Intensity greater than 130 |
| Bacteriostatic pores | Yellow | Intensity greater than 130 |
| Sluggish Oil Flow | Red | Intensity greater than 130 |
| Deeply Inflamed Pores | Bright white | Intensity greater than 130 |

FIG. 13B

SYSTEMS AND METHODS FOR ANALYZING SKIN CONDITIONS OF PEOPLE USING DIGITAL IMAGES

CROSS REFERENCE TO RELATED APPLICATIONS

The present application is a continuation of U.S. patent application Ser. No. 11/476,278, filed on Jun. 27, 2006 now U.S. Pat. No. 7,477,767, which is a continuation-in-part of U.S. patent application Ser. No. 11/232,452, filed on Sep. 20, 2005 now U.S. Pat. No. 7,454,046, the contents of which are incorporated herein by reference in their entireties.

FIELD OF THE INVENTION

The present invention relates generally to digital image acquisition, processing and analysis, and more particularly to analyzing skin conditions of people using digital images.

BACKGROUND INFORMATION

The human skin is sensitive to a variety of conditions and changes that may require long-term monitoring and care. Skin conditions such as acne, wrinkles, UV damage, and moles are common in a large number of people. Most of these conditions benefit from the use of one or more skin care products, often designed to target a specific condition. There are a variety of skin care products available today which are sold or administered to customers or patients. The products rely mainly on qualitative and highly subjective analysis of facial features and skin defects or ailments associated with the customers or patients. The effects of the skin care products may also be tested at a qualitative level, without a quantitative and objective proof of effectiveness.

With the recent advancements in digital imaging and microprocessor technology, the medical and healthcare industry are starting to find digital image processing and analysis helpful in the detection or diagnosis of defects or diseases on the surface of or inside the human body or other living organisms. Although several research projects have been carried out in the skin care industry to explore computer analysis of skin images, the technology of using digital images of a person's skin to evaluate a variety of skin conditions associated with the person is still primitive and in need of substantial development.

Visits to dermatologist offices and medical spas offering skin care products and treatment tend to be limited to a visual analysis of the patients' skin conducted by a doctor or other specialist, with rare instances of use of digital image processing technology to aid in the course of treatment. There are also no products available today that let patients evaluate their skin conditions while on the road, for example, at a beach while being exposed to UV radiation.

There is therefore a need for a method and system capable of analyzing a variety of skin conditions with the use of digital images.

There is also a need for a method and system for analyzing a variety of skin conditions with the use of portable devices equipped to acquire digital images of a person's skin.

SUMMARY OF THE INVENTION

In view of the foregoing, the present invention provides systems and methods for analyzing skin conditions using digital images.

In one exemplary embodiment, a white-light image and an ultraviolet ("UV") image of a portion of a body surface, such as a person's face, are acquired each of the white-light and UV images including a plurality of pixels, are acquired with an image acquisition device.

The image acquisition device may include, but is not limited to, film-based or digital cameras, wireless phones and other personal digital appliances ("PDAs") equipped with a camera, desktop and notebook computers equipped with cameras, and digital music players, set-top boxes, video game and entertainment units, and any other portable device capable of acquiring digital images and having or interacting with at least one white-light and UV light sources.

In accordance with the present invention, the white-light and UV images are analyzed to identify skin pixels. Information in the skin pixels is used to identify at least one skin condition. The skin conditions that may be detected and classified include, but are not limited to, skin tone, UV damage, pores, wrinkles, hydration levels, collagen content, skin type, topical inflammation or recent ablation, keratosis, deeper inflammation, sun spots, different kinds of pigmentation including freckles, moles, growths, scars, acne, fingi, erythema and other artifacts. Information in the skin pixels may also be used to perform feature measurements such as the size and volume of a lip, nose, eyes, ears, chins, cheeks, forehead, eyebrows, among other features.

In one exemplary embodiment, the skin pixels are identified by examining each pixel in the white-light and/or UV images to determine if the pixel has properties that satisfy predetermined criteria for skin pixels. Examination of the pixels in the white-light and UV images may include examining with reference to a skin map or skin mask, which, as generally used herein, is a virtual image, matrix or data group having a plurality of elements, each element corresponding to a pixel in the white-light or UV image.

In one exemplary embodiment, the white-light image is of a first color space, and at least one other white-light image is constructed by converting the original white-light image into at least one second color space. For each element in the skin mask, the corresponding pixel in each of the white-light images is examined with reference to predetermined criteria associated with a respective color space. A first value is assigned to an element in the skin mask if the corresponding pixel in each of the white-light images has pixel values that satisfy predetermined criteria for skin pixels associated with a respective color space, and a second value is assigned to an element in the skin mask if the corresponding pixel in any of the white-light images has pixel values that do not satisfy predetermined criteria for skin pixels associated with a respective color space. In a further exemplary embodiment, some of the elements in the skin mask are predefined as corresponding to non-skin features according to a coordinate reference. These elements are assigned the second value disregarding what values their corresponding pixels in the white-light images have.

After all elements of the skin mask have been assigned the first or second value, each pixel in any of the white-light and UV images that corresponds to an element having the first value in the skin mask would be identified as a skin pixel, and each pixel in any of the white-light and UV images that corresponds to an element having the second value in the skin mask would be identified as a non-skin pixel. Pixels that are identified as non-skin pixels are not considered in obtaining results for the at least one skin conditions.

In one aspect of the invention, each skin pixel of the white-light and UV images includes values associated with three color channels, and results obtained for UV damage are computed based on values associated with one of the three color channels in the skin pixels of the first UV image.

In another aspect, a standard deviation is computed using values associated each of the three color channels in the skin pixels of the white-light image, and the standard deviations for the three color channels, or their average value, is used as a quantitative measure for the skin tone of the skin under analysis.

In a further aspect of the present invention, a color value and an intensity value associated with each of the skin pixels in the UV image are computed and examined with reference to at least one look-up table to determine if they correspond to a specified skin condition. For each skin pixel in the UV image that is determined to correspond to a specified skin condition, surrounding skin pixels are examined for the specified skin condition to determine a size of a skin area having the specified skin condition. Statistical results such as a number and/or distribution of the areas having one or more specified skin conditions can also be provided.

In one exemplary embodiment, the results associated with at least one selected skin condition can be displayed on a user interface using an image having the at least one type of skin condition highlighted, and/or with at least one number or chart quantifying the skin condition. In a further exemplary embodiment, both current and prior results associated with at least one selected skin condition for the person are displayed next to each other for comparison. The results compared may include statistical results or other data analysis quantifying the skin conditions that are identified and classified for the subject.

In this exemplary embodiment, an alignment of the subject's portion of a body surface being analyzed, such as the subject's face, is performed prior to the comparison. The alignment ensures that images acquired for generating the current results are aligned with the images acquired for generating the previous results for the same subject. A grid is used to align portions of the body surface of the subject being analyzed, such as the subject's nose, eyes, and mouth, with the same portions displayed on previous images acquired for generating previous results for the same subject.

According to these and other exemplary embodiments of the present invention, the system for analyzing skin conditions generally includes an image acquisition device, at least one light source coupled to the image acquisition device, and a computing device coupled to the image acquisition device and to the light source, and a display coupled to the computing device. The computing device includes modules for carrying out different aspects of the method for analyzing skin conditions as summarized above and described in more detail below. The modules may be in hardware or software or combinations of hardware and software. In one exemplary embodiment, the computing device includes a microprocessor and a memory device coupled to the microprocessor, and the modules include software programs stored as program instructions in a computer readable medium associated with the memory device.

In one exemplary embodiment, the image acquisition device coupled with at least one light source may be connected to the computing device via a wired or wireless network. Accordingly, images acquired by the image acquisition device coupled with at least one light source may be sent to the computing device via a network for analysis. The results of the analysis may then be sent to a user of the image acquisition device via a number of communication means, including, but not limited to, email, fax, voice mail, and surface mail, among others. Alternatively, the results may be posted on a web site or another medium for later retrieval by the user.

In another exemplary embodiment, the image acquisition device coupled with at least one light source may include a portion or all of the modules for carrying out different aspects of the invention as summarized above and described in more detail herein below. In this exemplary embodiment, the images acquired by the image acquisition device may be analyzed on the device itself, thereby eliminating the need for the images to be sent to a separate computing device connected to the image acquisition device. Alternatively, a partial analysis may be performed in the image acquisition device and the images may still be sent to a separate computing device for further analysis.

The image acquisition device and the systems of the present invention may be used at a number of locations, including doctor officers, medical spas and other health care facilities, open spaces such as parks and beaches, inside transportation vehicles such as cars and airplanes or at any other location where it is desired to acquire information about one's skin.

Advantageously, the present invention enables doctors and other skin care specialists to obtain quantitative measures of a variety of skin conditions. The quantitative measures may be acquired before or after a skin care treatment to evaluate the suitability of the treatment for a given condition. In addition, the present invention enables patients to obtain rapid assessments of their skin at any location, thereby assisting them in the proper care and maintenance of their skin on a daily basis.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which:

FIG. 9A is a flowchart illustrating process steps for identifying skin pixels in the digital images according to an exemplary embodiment of the present invention;

FIG. 9B is a table listing exemplary ranges of pixels values for different color channels for each of a plurality of color spaces that are used to identify skin pixels;

FIG. 13B is a table listing exemplary pixel colors and intensities associated with different skin conditions;

DETAILED DESCRIPTION OF EMBODIMENTS OF THE INVENTION

Generally, in accordance with exemplary embodiments of the present invention, systems and methods are provided for identifying and analyzing skin conditions in a person based on an digital images of the person's skin. Skin conditions that may be identified and analyzed by the systems and methods of the present invention include, but are not limited to, skin tone, UV damage, pores, wrinkles, hydration levels, collagen content, skin type, topical inflammation or recent ablation, keratosis, deeper inflammation, sun spots, different kinds of pigmentation including freckles, moles, growths, scars, acne, fungi, erythema and other artifacts. Information in the skin pixels may also be used to perform feature measurements such as the size and volume of a lip, nose, eyes, ears, chins, cheeks, forehead, eyebrows, among other features.

Figure 1:
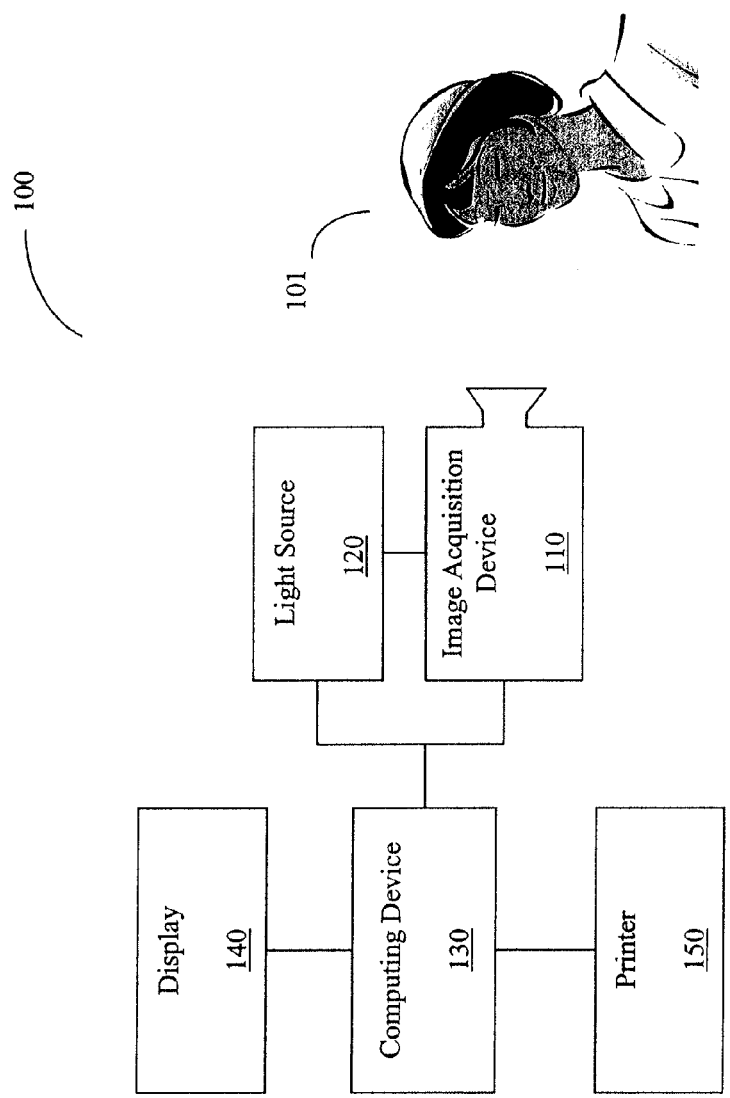
FIG. 1 is a simplified block diagram of a system for analyzing skin conditions according to embodiments of the present invention.

FIG. 1 depicts a simplified block diagram of a system 100 for analyzing skin conditions according to an exemplary embodiment of the present invention. As shown in FIG. 1, system 100 includes image acquisition device 110, at least one light source 120 coupled to image acquisition device 110, computing device 130 coupled to image acquisition device 110 and to at least one light source 120 either directly or through image acquisition device 110, display 140 coupled to computing device 130, and optionally printer 150 also coupled to computing device 130. System 100 is configured to acquire digital images of subject 101, such as a person's face, and to process the digital images to obtain results related to at least one skin condition associated with the person.

Figure 2A:
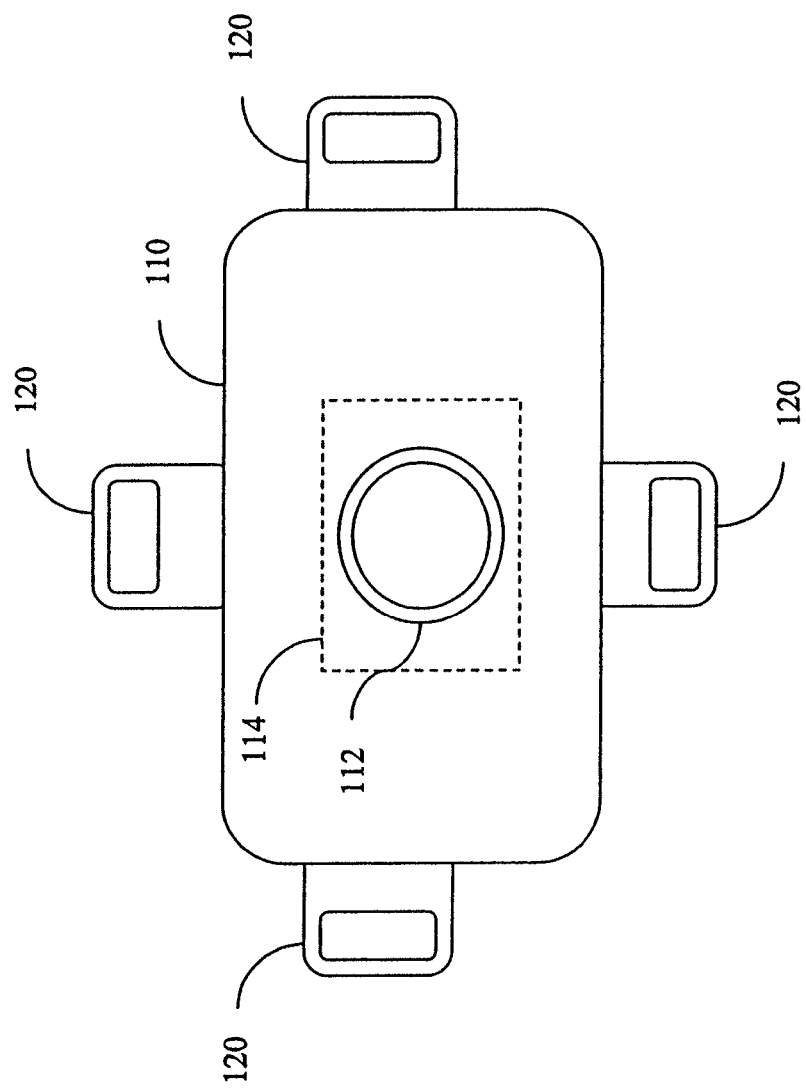
FIG. 2A is a line drawing of an exemplary image acquisition device in the system shown in FIG. 1 according to an exemplary embodiment of the present invention.

In one exemplary embodiment, as shown in FIG. 2A, image acquisition device 110 is part of acquisition device 200 having image sensor 112 and optical assembly 114 in front of image sensor 112 and configured to form an image of subject 101 on image sensor 114. Image sensor 114 may include, for example, 5-15 or more million Mega pixels made of photon detecting devices, such as charge-coupled devices ("CCD"), CMOS devices or charge-injection devices ("CID"), among others. Each pixel includes three sub-pixels corresponding to three different color channels.

Figure 2B:
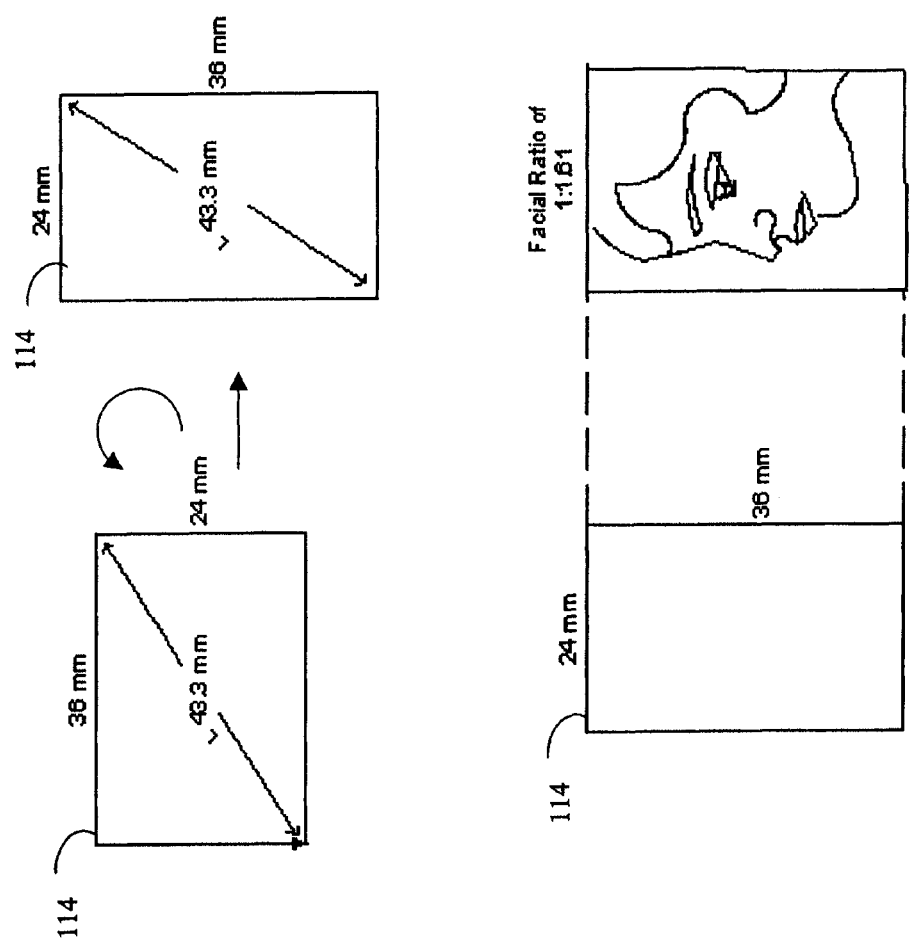
FIG. 2B is a line drawing showing an aspect ratio of a sensor in the exemplary image acquisition device of FIG. 2A being adjusted to accommodate the dimensions of a portion of a person's body surface to be imaged.

The number of pixels used in image sensor 114 to capture the white-light and UV images can be varied or held fixed. As shown in FIG. 2B, image sensor 114 is rotated to have its aspect ratio changed from 1.5:1 (36:24) to 1:1.5 (24:36) in order to capture the whole length of a person's face and to more accurately match a facial ratio of 1:1.61. In a further exemplary embodiment, image sensor 114 may have a variable number of pixels.

FIG. 2A also shows a plurality of light sources 120 as parts of acquisition device 200, including, for example, two flash light sources 120 on two sides of acquisition device 200, flash light source 120 on top of acquisition device 200, and optionally another flash light source 120 at the bottom of acquisition device 200. Having more than one flash light sources 120 allows more uniform exposure of subject 101 to light during imaging.

Different light sources may be configured to emit different colors or wavelengths of light, but the number of light sources 120 and their positions in system 100 can be varied without affecting the general performance of the system. In one exemplary embodiment, a portion of light sources 120 may be configured to illuminate subject 101 with white light, and another portion of light sources 120 may be configured to emit ultraviolet ("UV") light. Other light sources, such as the sun and surrounding lights may also be used without deviating from the principles and scope of the present invention.

Acquisition device 200 may also include other parts or components that are not shown, such as a shutter, electronics for allowing computing device 130 to control the shutter, flashings from light sources 120, and electronics for outputting captured images to computing device 130 for analysis, among others. To prevent saturation of the pixels in image sensor 114, acquisition device 200 may also include anti-blooming devices. At a minimum, acquisition device 200 may include image acquisition device 110 and at least one light source 120.

Figure 2C:
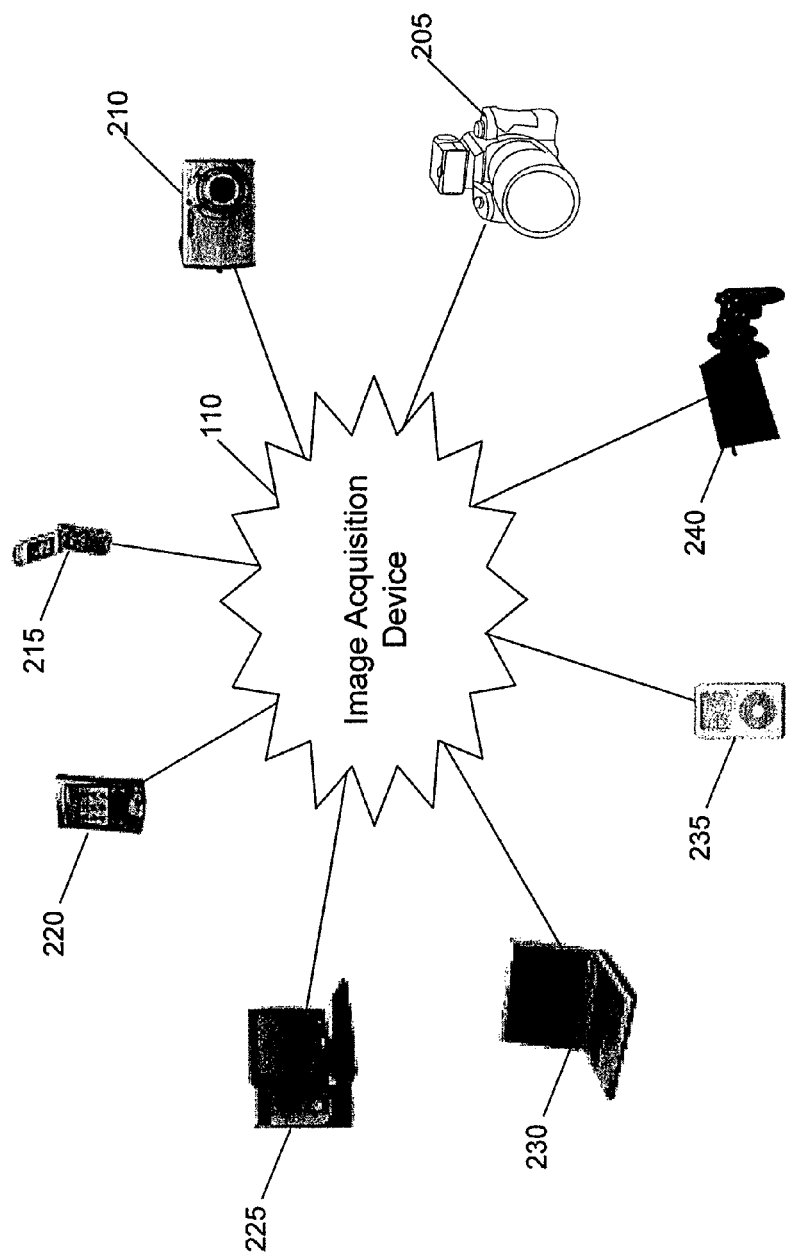
FIG. 2C is a schematic of exemplary image acquisition devices that can be converted into the image acquisition device shown in FIG. 2A.

Acquisition device 200, as shown in FIG. 2C, may be converted from a number of portable image acquisition devices 110, including, but not limited to, film-based camera 205 or digital camera 210, wireless phone 215 and other personal digital appliances ("PDAs") equipped with a camera such as PDA 220, desktop computer 225 and notebook computer 230 equipped with cameras, and digital music player 235, set-top boxes, video game and entertainment units 240, and any other device capable of acquiring digital images and having or interacting with at least one light source, such as light sources 120 on the top, bottom, and on the sides of image acquisition device 110.

Figure 2D:
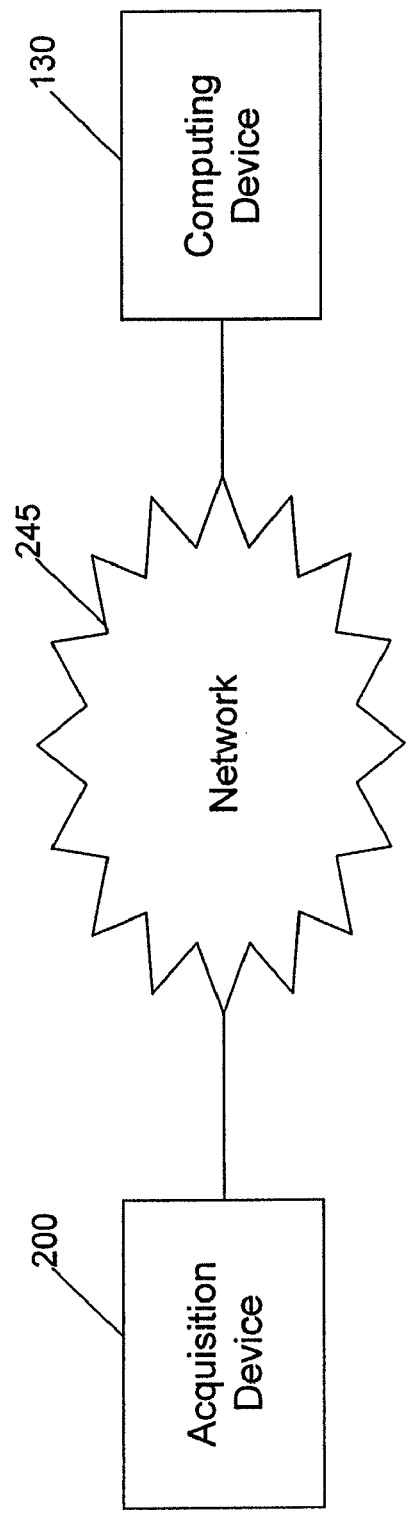
FIG. 2D is a schematic of an exemplary embodiment of the present invention showing an acquisition device coupled to a computing device via a network.

In one exemplary embodiment, shown in FIG. 2D, acquisition device 200 may be connected to computing device 130 via wired or wireless network 245. Accordingly, images acquired by acquisition device 200 are sent to computing device 130 via network 245 for analysis. The results of the analysis may then be sent to a user of acquisition device 200 via a number of communication means, including, but not limited to, email, fax, voice mail, and surface mail, among others. Alternatively, the results may be posted on a web site or another medium (such as a database) for later retrieval by the user.

In another exemplary embodiment, acquisition device 200 may include a portion or all of the modules for carrying out different aspects of the invention as summarized above and described in more detail herein below. In this exemplary embodiment, the images acquired by acquisition device 200 may be analyzed on the device itself, thereby eliminating the need for the images to be sent to separate computing device 130 connected to acquisition device 200 via network 245. Alternatively, a partial analysis may be performed in acquisition device 200 and the images may still be sent to separate computing device 130 for further analysis.

Light sources 120 that are on the top and at the bottom of acquisition device 200 may be white light sources and light sources 120 on the sides of acquisition device 200 may be UV light sources. The white light sources can be conventional off-the-shelf flash light sources, such as flash light source 300 shown in FIG. 3. Each of UV light sources 120 can be one converted from light source 300 by changing low-pass filter 310 in front of light source 300 into UV filter 310.

Figure 3A:
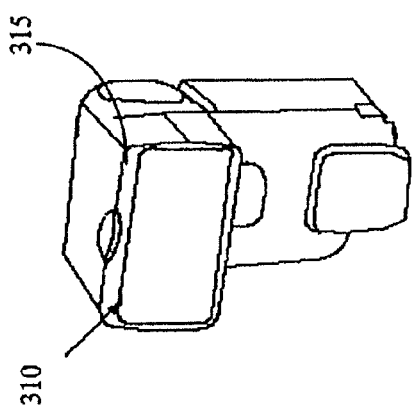
FIG. 3A is a line drawing of a flash light source in the system shown in FIG. 1 according to an exemplary embodiment of the present invention.
Figure 3B:
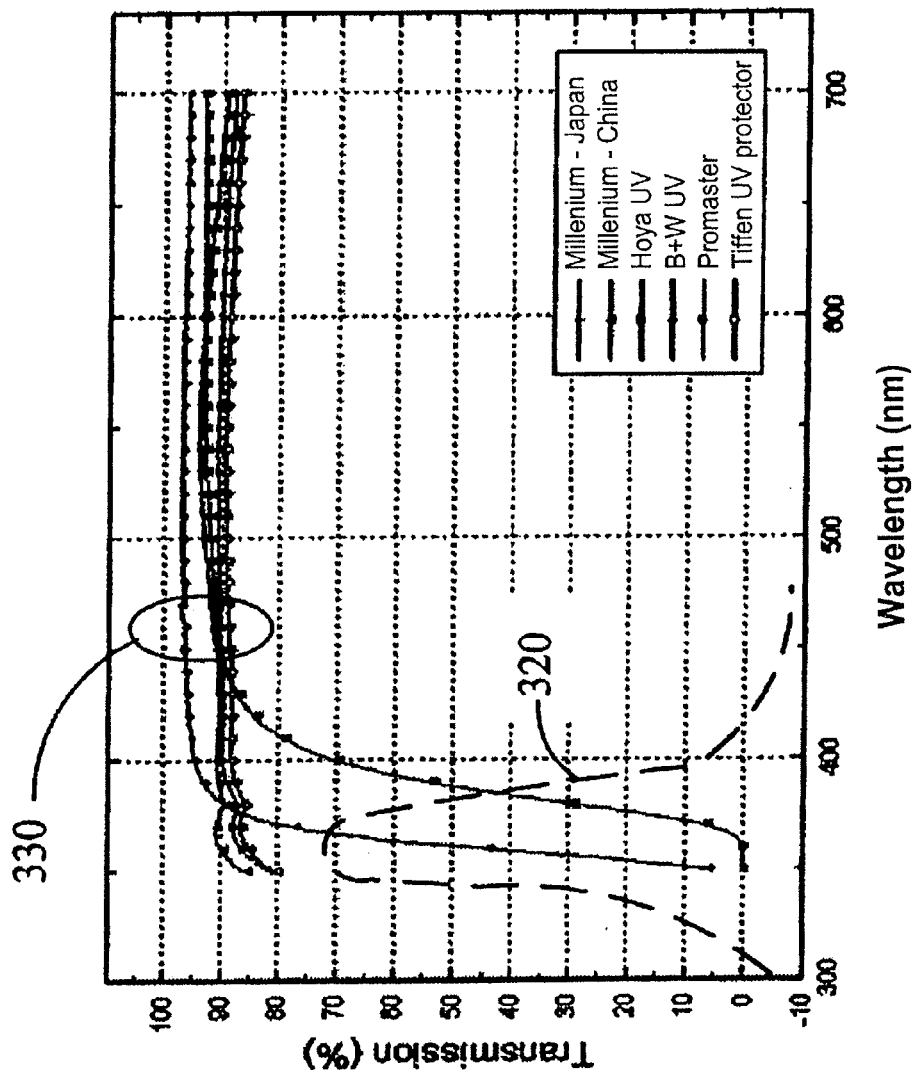
FIG. 3B is a chart illustrating a transmission spectrum of a UV bandpass filter as compared with transmission spectra of other white-light filters.

In one exemplary embodiment, as shown in FIGS. 3A-B, UV filter 310 is a bandpass filter that provides transmission spectrum 320 having a width of about 50 nm and a peak wavelength of about 365 nm. In comparison, low-pass filter 310 would provide a transmission spectrum, such as one of spectra 330 shown in FIG. 3B, that drops sharply to near zero in the UV wavelength range and stays relatively flat in the visible wavelength range. In addition to the white-light and UV filters, some or all of light sources 120 may also have infrared absorbing filters 315 installed. Infrared absorbing filters 315 help to prevent heat from light sources 120 to be applied to subject 101 by filtering out wavelengths greater than, for example, 700 nm.

Figure 4:
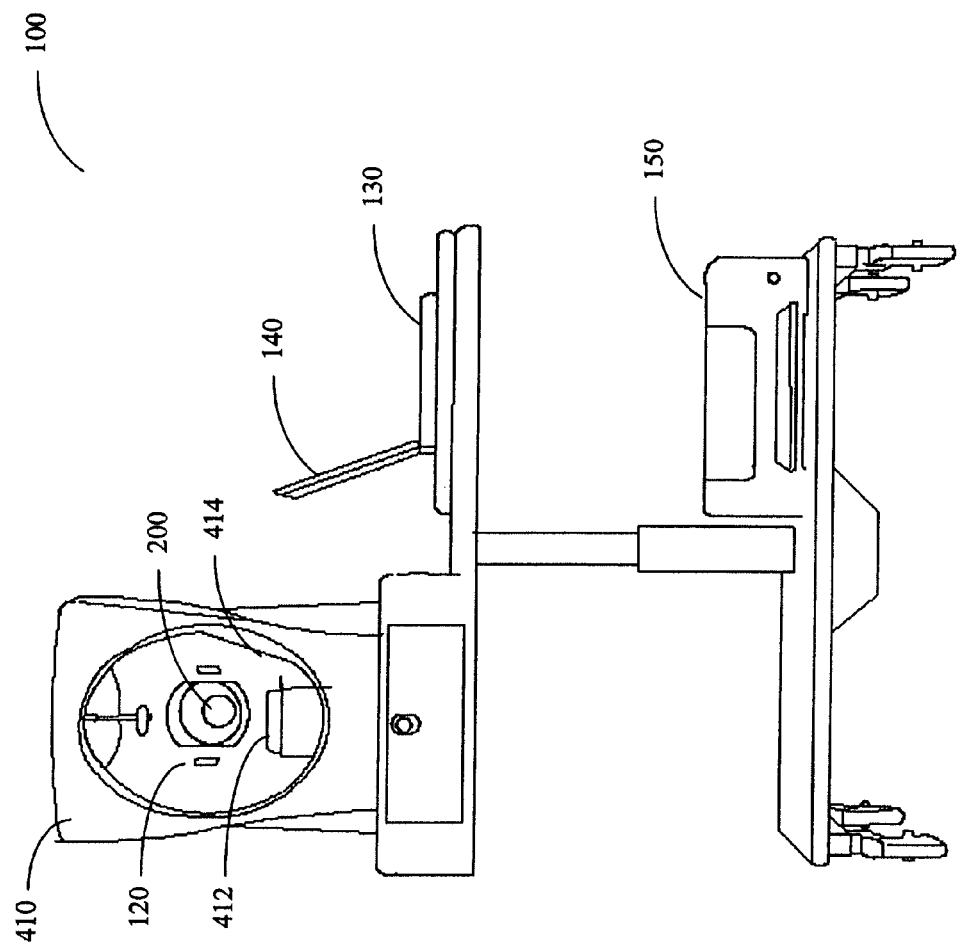
FIG. 4 is a line drawing of an exemplary setup for the system illustrated in FIG. 1 according to an exemplary embodiment of the present invention.

Acquisition device 200 may be installed in an imaging box, such as box 410 shown in FIG. 4, which illustrates an exemplary setup of system 100. Imaging box 410 helps to prevent ambient light from entering sensor 212 and interfering with the analysis of skin conditions. An example of such an imaging box is the Facial Stage DM-3 commercially available from Moritex Corporation, of Tokyo, Japan. FIG. 4 also shows acquisition device 200 placed near a center in the back of box 410, light sources 120 on top and sides of optical assembly 214, and a pedestal or chin rest 412 near opening 414 of imaging box 410 on which subject 101 can rest and stay still during imaging acquisition. FIG. 4 also shows, as an example, computing device 130 and display 140 as parts of a laptop computer and printer 150 placed under the laptop computer.

Figure 5:
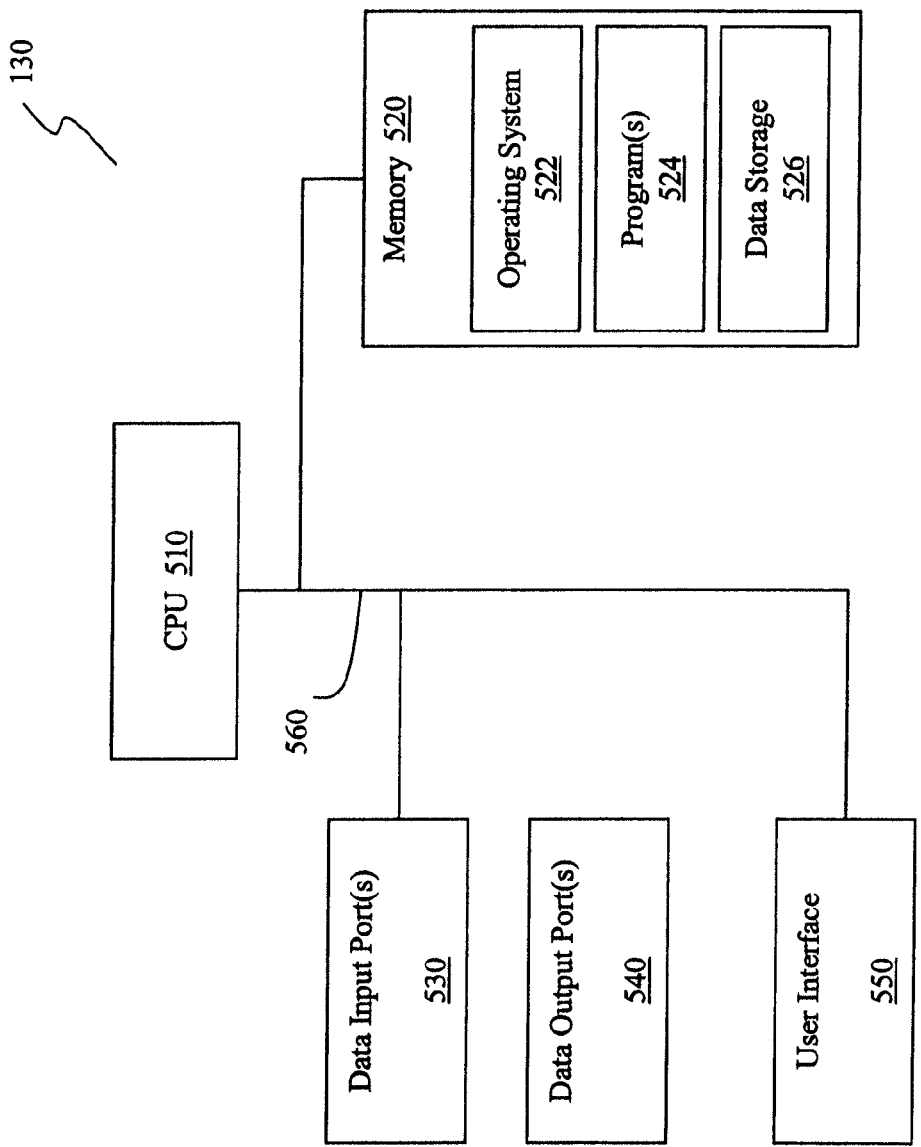
FIG. 5 is a simplified block diagram of a computing device in the system illustrated in FIG. 1 according to an exemplary embodiment of the present invention.

In one exemplary embodiment of the present invention, as shown in FIG. 5, computing device 130 can be any computing device having a central processing unit ("CPU") such as CPU 510, memory unit 520, at least one data input port 530, at least one data output port 540, and user interface 550, interconnected by one or more buses 560. Memory unit 520 preferably stores operating system software 522 and other software programs including program 524 for analyzing skin conditions using digital images. Memory unit 520 further includes data storage unit 526 for storing image data transferred from acquisition device 200 through one of the at least one data input port 530 and for storing prior skin condition results associated with subject 101 and other data or data structures generated during current execution of program 524, as discussed below.

Program 524 may be organized into modules which include coded instructions and when executed by CPU 510, cause computing device 130 to carry out different aspects, modules, or steps of a method for automatically identifying a person according to the present invention. All or part of memory unit 520, such as database 526, may reside in a different geographical location from that of CPU 510 and be coupled to CPU 510 through one or more computer networks.

Figure 6:
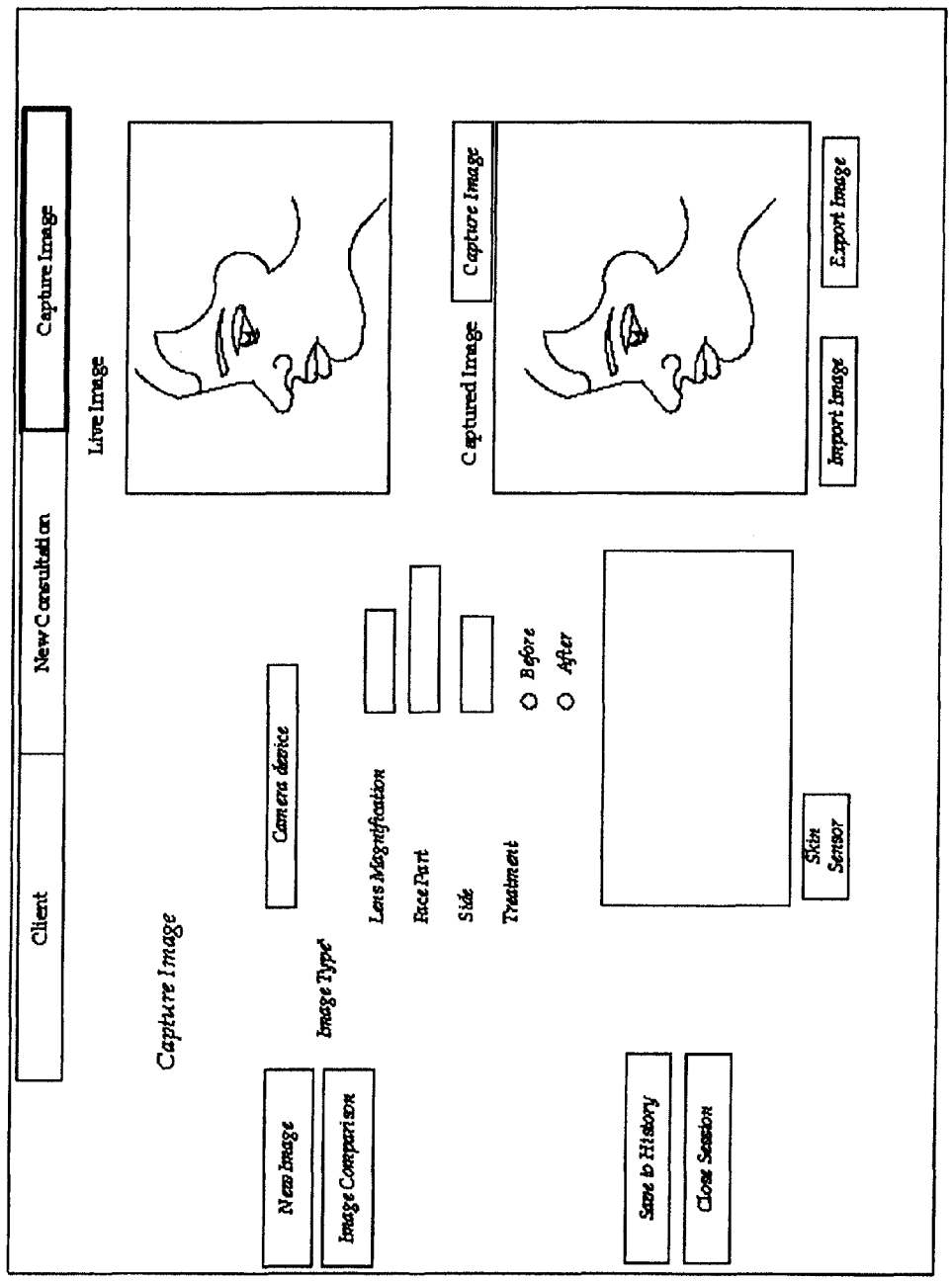
FIG. 6 is a line drawing of a user interface associated with the computing device illustrated in FIG. 1 according to an exemplary embodiment of the present invention.

Program 524 may also include a module including coded instructions, which, when executed by CPU 510, cause computing device 130 to provide graphical user interfaces ("GUI") for a user to interact with computing device 130 and direct the flow of program 524. An example of a GUI for capturing digital images of subject 101 is illustrated in FIG. 6 as GUI 600.

Figure 7A:
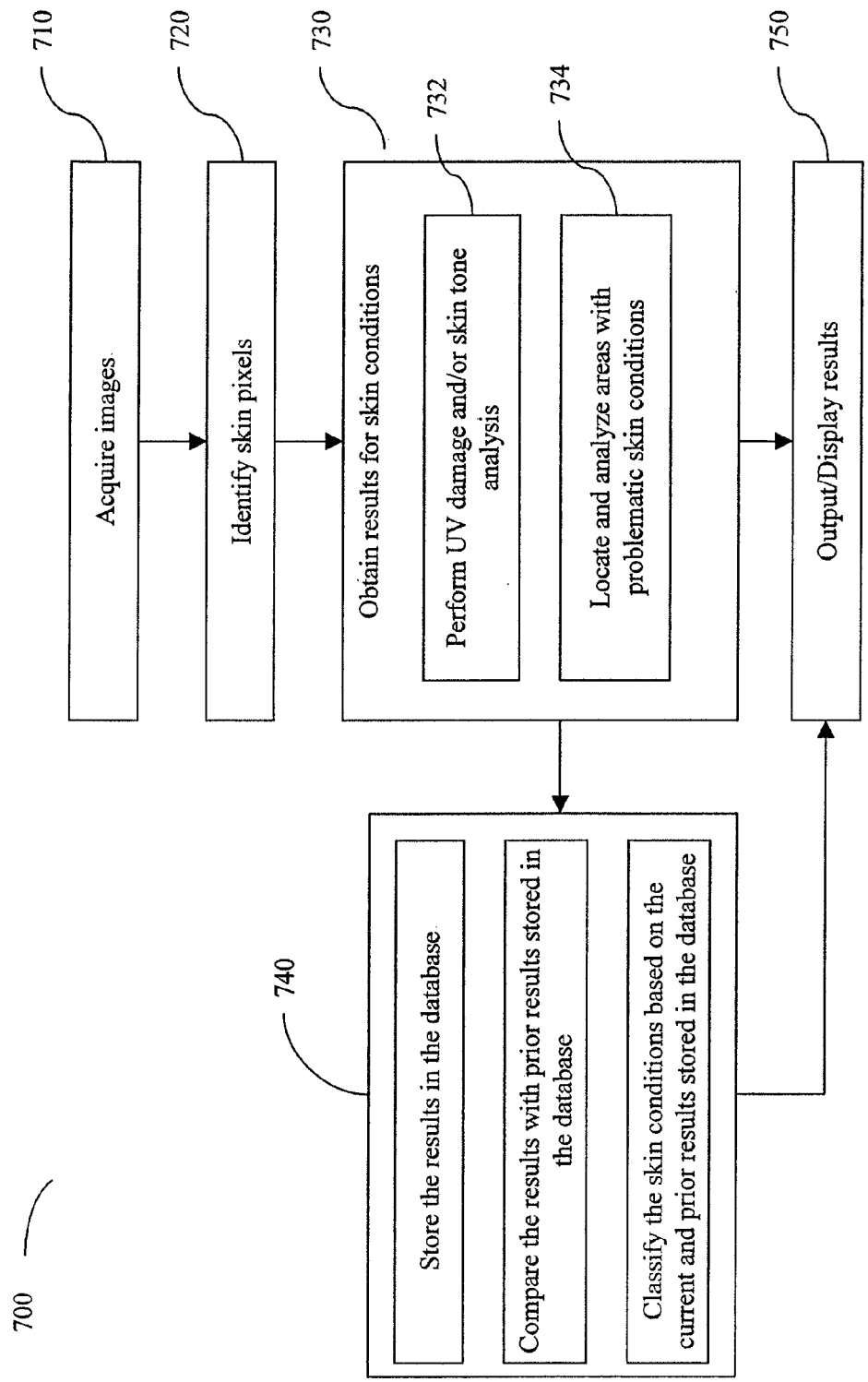
FIG. 7A is a flowchart illustrating a method for analyzing skin conditions using digital images according to an exemplary embodiment of the present invention.

Referring now to FIG. 7A, a flowchart illustrating method 700 for analyzing skin conditions using digital images according to an exemplary embodiment of the present invention is provided. As shown in FIG. 7A, method 700 includes module 710 for acquiring digital images of subject 101. In one exemplary embodiment, the acquired digital images include a first white-light image and a first UV image. Each of the first white-light and UV images includes a plurality of pixels. Each pixel in the first white-light or UV image corresponds to a pixel in sensor 114.

In one exemplary embodiment, each of the pixels in sensor 114 includes three sub-pixels corresponding to three color channels for sensing three color components in a received light signal. Thus, each pixel in the white-light and UV image includes values associated with the three color channels, which are referred to sometimes in this document as pixel values. The pixel values may range, for example, between 0 and 255.

The images captured by sensor 114 and the images used by computing device 130 may be of different formats. An appropriate image conversion software may be used by computing device 130 to convert an image format, such as BMP, TIFF, or FITS, used by acquisition device 200 to another image format used by computing device 130. The images from acquisition device 200, after any conversion, may be initially processed by computing device 130 using conventional techniques for dark current and/or intensity correction, and image manipulation or enhancement, before being used for analyzing skin conditions.

The images may also be initially processed to have some pixels, such as those at the four corners of a rectangular image, taken out because it may be easy to tell that they have collected information from surrounding objects, instead of from subject 101. Thus, each of the acquired digital images, such as the first white-light and UV images, is referred to as either the original image acquired by acquisition device 200 or an image derived from the original image after one or more format or color space conversions, and/or after some initial processing such as those stated above.

Generally, subject 101, or part of it, that is captured in the images include both skin and non-skin portions or features, such as hair, clothing, eyes, lips, nostrils, etc. Furthermore, some of the objects surrounding subject 101 may also be captured in the images. Therefore, the pixels in the first white-light and UV images often include both skin pixels, meaning pixels that have captured signals from the skin portions of subject 101, and non-skin pixels, meaning pixels that have captured signals from non-skin features of subject 101 or from objects surrounding subject 101.

Since non-skin pixels may interfere with the analysis of skin conditions, method 700 further includes module 720 for identifying, on a pixel by pixel basis, skin pixels and/or non-skin pixels in the first white-light and/or UV image, and module 730 for obtaining results associated with at least one skin condition using only information in the skin pixels in the first white light and UV images.

Module 730 may include sub-modules 732 for performing UV damage and skin tone analysis, and sub-modules 734 for locating and quantifying localized skin conditions, such as one or more types of acne, pores, wrinkles, sun spots, different kinds of pigmentation including freckles, moles, growths, scars, acne, and fungi, growths, etc. Module 730 may also include sub-modules (not shown) for examining other skin conditions, such as skin tone, UV damage, hydration levels, collagen content, skin type, topical inflammation or recent ablation, keratosis, deeper inflammation, erythema and/or any or the other skin conditions identifiable using the information in one or both of the white-light and UV images according to knowledge known to those familiar with the art. Module 730 may also include sub-modules for performing feature measurements such as the size and volume of a lip, nose, eyes, ears, chins, cheeks, forehead, eyebrows, among other features.

Method 700 further includes module 740 in which module 700 interacts with database 526 to store the current results in database 526, compare the current results with prior results associated with the same subject 101, and/or to classify the skin conditions based on the comparison. Method 700 further includes module 750 for outputting and/or displaying results from the analysis. The results compared may include statistical results or other data analysis quantifying the skin conditions that are identified and classified for the subject.

Figure 7B:
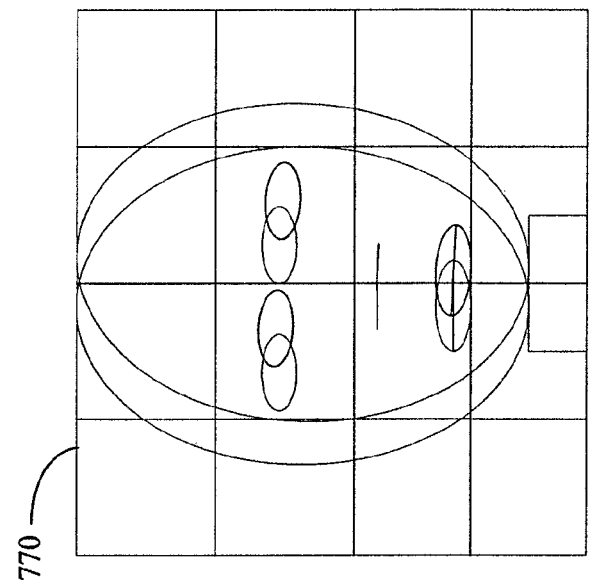
FIG. 7B is a line drawing illustrating the alignment of a subject's face performed prior to acquiring current results and comparing them with previous results at step 740 of the flowchart of FIG. 7A.
Figure 7B:
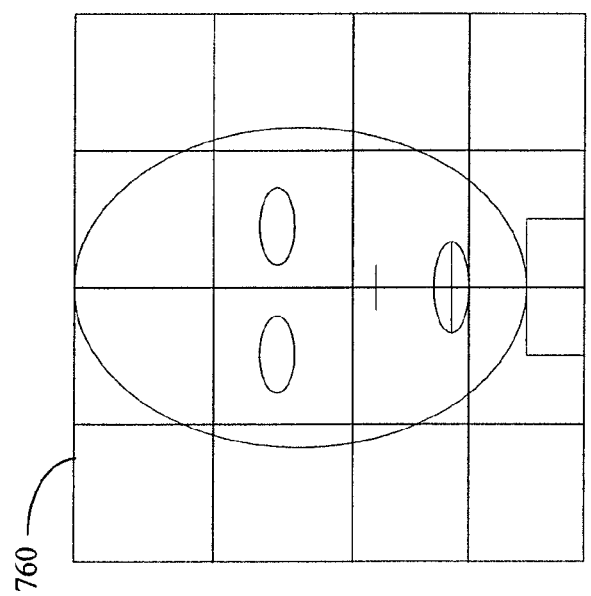

Prior to generating the current results, an alignment of the subject's portion of a body surface being analyzed, such as the subject's face, is performed as shown in FIG. 7B. The alignment ensures that images acquired for generating the current results are aligned with the images acquired for generating the previous results for the same subject. A grid is used to align portions of the body surface of the subject being analyzed, such as the subject's nose, eyes, and mouth, with the same portions displayed on previous images acquired for generating previous results for the same subject.

For example, image 760 shows an image of the subject's face acquired for generating the previous results being displayed on a grid for more accurate placement of the face's features, such as the subject's eyes, nose, and mouth. Image 770 shows the same image on a grid overlying an image being acquired at a later time for generating current results for the subject. The two images are aligned to guarantee that the results obtained at the two different times reflect the same positioning of face features at the two times.

Figure 8A:
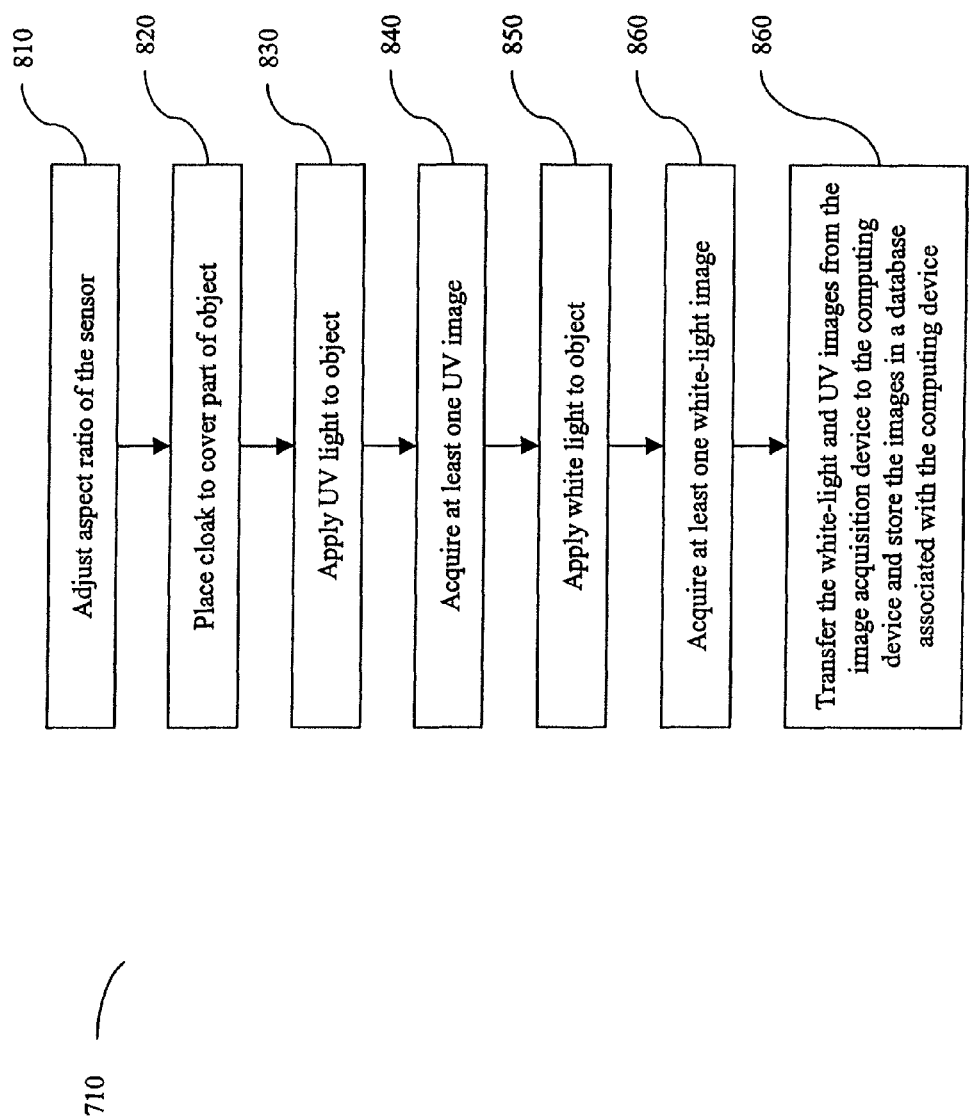
FIG. 8A is a flowchart illustrating process steps for acquiring digital images of a body surface according to an exemplary embodiment of the present invention.

FIG. 8A illustrates process steps in module 710 for acquiring the digital images of subject 101 according to one exemplary embodiment of the present invention. As shown in FIG. 8A, module 710 includes step 810 in which the aspect ratio of sensor 114 is adjusted according to dimensions of subject 101, and step 820 in which a light absorbing cloak is placed over subject 101 to cover as much as possible non-skin portions of subject 101.

Figure 8B:
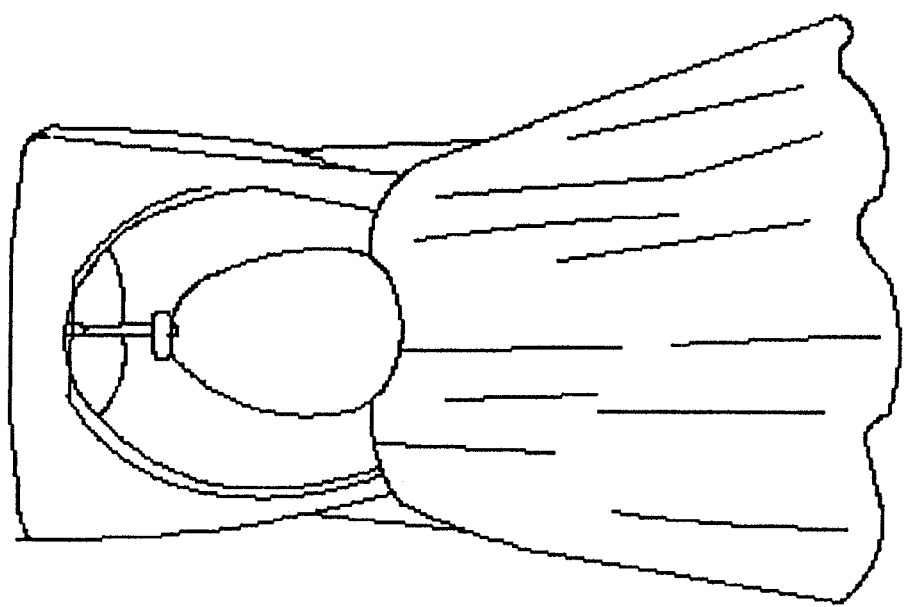
FIG. 8B is a line drawing of a person in front of an image acquisition device wearing a cloak according to an exemplary embodiment of the present invention.

For example, as illustrated in FIG. 8B, a person in front of imaging box 410 to have his or her face imaged by acquisition device 200 may have his or her shoulders and chest covered by cloak 830 such that the person's clothing would not be captured by acquisition device 200 and that the person is allowed to reach full fluorescence under UV illumination. In one exemplary embodiment, cloak 830 is made of one or more layers of light absorbing fabric such as one known as Tuf-Flock or Tough Lock, which is a vinyl backed velour that can be purchased at photography specialty stores.

Module 710 further includes step 830 in which UV light sources 120 are turned on to send a flash of UV light to subject 101. The flash of UV light should include a band of UV wavelengths the can cause the skin associated with subject 101 to fluoresce, as illustrated in FIG. 3B. At about the same time, the shutter of acquisition device 200 camera is opened at step 840 so that the first UV image is captured by sensor 114.

The application of UV light to dermatology and health care has been researched and utilized in order to aid in the detection and diagnosis of a number of afflictions or skin disorders. Given that most living organisms fluoresce upon excitation through the absorption of light, a phenomenon known as auto-fluorescence, it has been shown that different organisms can be classified through their Stokes shift values. Stokes shift, as generally used herein, is the difference between peak wavelength or frequency of an absorption spectrum and peak wavelength or frequency of an emission spectrum. Furthermore, UV light can penetrate deeper into the skin than visible light, making it possible to detect subsurface skin conditions (i.e., skin conditions below the surface) and allowing for early diagnosis of melanoma and other skin cancer symptoms.

Therefore, by acquiring the first UV image, the embodiments of the present invention are able to combine the knowledge of auto-fluorescence of the skin and image processing technologies to provide automated detection and analysis of subsurface skin conditions, as described in more detail below.

Module 710 further includes step 850 in which white-light sources 120 are turned on to send a flash of white light to subject 101. The flash of white light preferably has wavelengths that span across a full spectrum of visible light or a substantial portion of it. At about the same time, the shutter of acquisition device 200 is opened at step 860 so that the first white-light image is captured by sensor 114.

Module 710 further includes step 870 in which the first white-light and UV images are transferred from acquisition device 200 into computing device 130 using conventional means and stored in database 526 for subsequent processing, and in which appropriate image conversion and/or initial processing steps are performed as discussed above.

In module 720, skin pixels in the first white-light and UV images are identified by examining each pixel in the first white-light and/or UV image to determine if properties of the pixel satisfy predefined criteria for skin pixels, according to one embodiment of the present invention. The properties of a pixel may include the pixel values, the pixel's position in the image, pixel values of one or more corresponding pixels in one or more other images (as discussed below), and/or its relationship with a skin map or skin mask.

As shown in FIG. 9A, module 720 includes step 810 in which each pixel in the first white-light image is examined to determine if the pixel values associated therewith satisfy a first set of predefined criteria for skin pixels. The criteria for skin pixels may be different for different color spaces, as illustrated in FIG. 9B, which lists, for each of a plurality of color spaces, ranges of values associated with different color channels for likely skin pixels.

For example, assuming the first white-light image being in a first color space, such as the red-green-blue ("RGB") color space, pixels that have the red channel (channel 1) values in the range of 105-255, the green channel (channel 2) values in the range of 52-191, and the blue channel (channel 3) values in the range of 32-180 are likely to be skin pixels. Thus, as shown in FIG. 10($a$), after examining the pixels in first white-light image 1010, part of the pixels in first white-light image 1010 are considered to be likely skin pixels, as illustrated by the white blocks in FIG. 10($a$), and the rest of the pixels in first white-light image 1010 are determined to be non-skin pixels, as illustrated by the black blocks in FIG. 10($a$).

Figure 10:
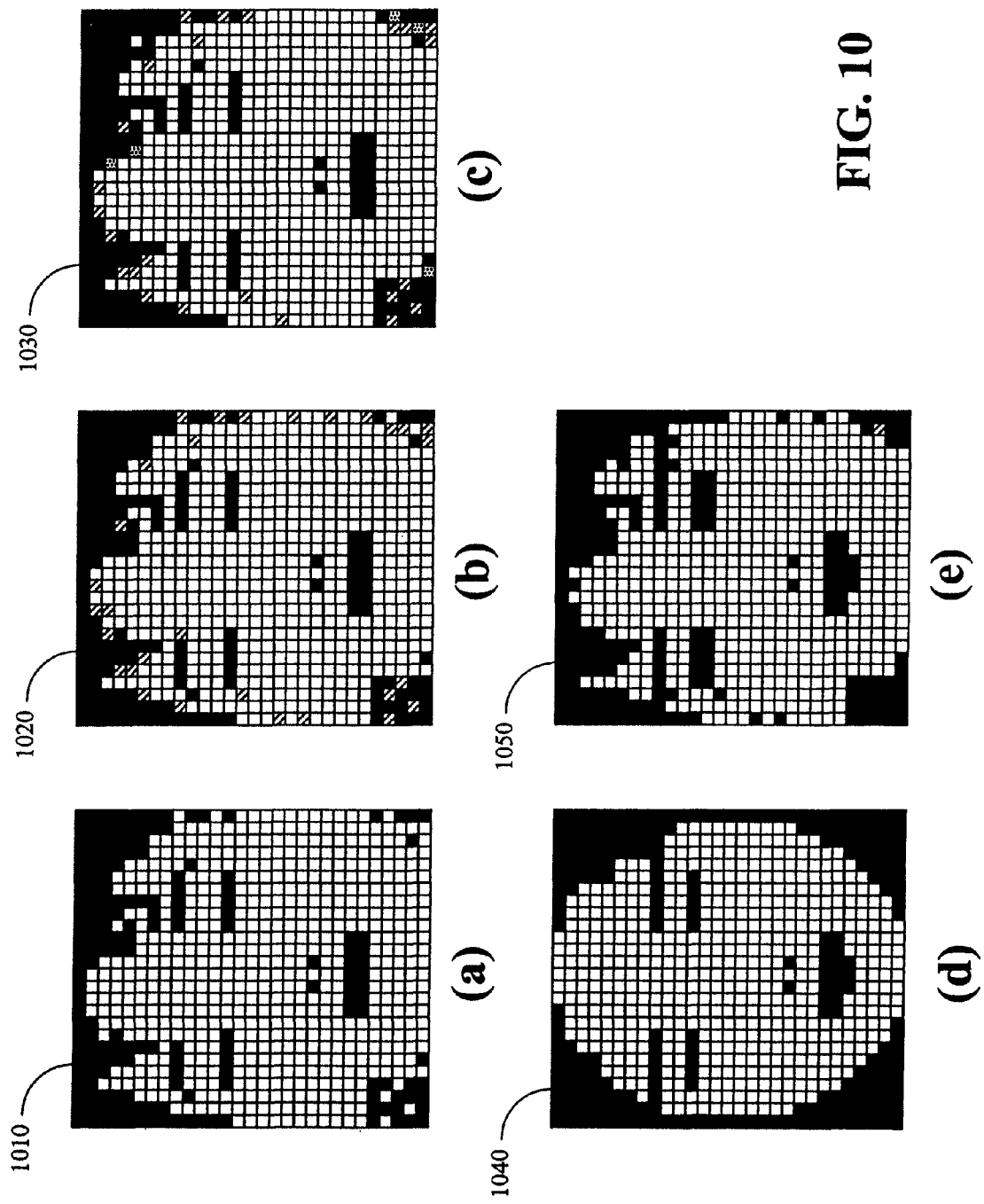
FIGS. 10(a) to 10(e) are simplified block diagrams illustrating a method for generating a skin mask according to an exemplary embodiment of the present invention.

To be more accurate in identifying the skin pixels, module 720 further includes step 820 in which first white-light image 1010 is converted to at least one other white-light image in at least one other color space, such as white-light image 1020 in a second color space illustrated in FIG. 10($b$), and white-light image 1030 in a third color space illustrated in FIG. 10($c$). Each pixel in the at least one other white-light image corresponds to a respective pixel in the first white-light image. The first, second, and third color spaces can be different ones selected from commonly known color spaces, such as the RGB, YIQ, LAB, YcBcR, and HSV color spaces, and/or any proprietary color spaces.

Module 720 further includes step 830 in which, for each of the at least one other white-light images, the pixels corresponding to the likely skin pixels in the first white-light image 1010 are further examined against criteria for skin pixels associated with the respective color space. For example, in second white-light image 1020, all pixels corresponding to non-skin pixels in first white-light image 1010 are deemed to be non-skin pixels and are illustrated in FIG. 10($b$) as black blocks, and pixels corresponding to likely skin pixels in first white-light image 1010 are further examined against criteria for skin pixels associated with the second color space. As a result, more pixels would be determined as non-skin pixels, which are shown in FIG. 10($b$) as blocks with stripes. The rest of the pixels in second white-light image 1020 are considered to be likely skin pixels and are illustrated by the white blocks in FIG. 10($b$).

Furthermore, in third white-light image 1030, all pixels corresponding to non-skin pixels in second white-light image 1020 are deemed to be non-skin pixels and are illustrated in FIG. 10($c$) as black blocks and blocks with stripes, and pixels corresponding to likely skin pixels in second white-light image 1020 are further examined against criteria for skin pixels associated with the third color space. As a result, more pixels would be determined as non-skin pixels, which are shown in FIG. 10($c$) as blocks with dots. The rest of the pixels in third white-light image 1020 are considered to be likely skin pixels and are illustrated by the white blocks in FIG. 10($c$). This process may continue until a last one of the at least one other white-light image (the last white-light image) is examined.

To be even more accurate in identifying the skin pixels and to make sure that non-skin pixels are not considered in analyzing the skin conditions, module 720 may include further step 840 in which coordinate reference 1040, such as the one shown in FIG. 10($d$), is used to classify more of the likely skin pixels as non-skin pixels. Coordinate reference 1040 may be pre-stored template together with a plurality of other coordinate reference or templates in database 526 in memory unit 520 of computing device 130, and selected as being a suitable one for subject 101.

Coordinate reference 1040 defines certain pixels in any of the white-light images as non-skin pixels (shown as black blocks in FIG. 10($d$)) based on their coordinates or positions in the image. So if any of the likely skin pixels in the last white-light image have coordinates that are defined as coordinates for non-skin features in coordinate reference 1040, these pixels are determined to be non-skin pixels. The rest of the like skin pixels in the last white-light image are finally identified as skin pixels, and all of the pixels in each of the other white-light images or the UV image that correspond to the skin pixels in the last white-light image are also identified as skin pixels. The rest of the pixels in each of the white-light or UV images are considered as non-skin pixels.

To help identify skin pixels in all of the images of subject 101 during subsequent processing, module 720 may include further step 850 in which a skin map or skin mask is generated. In one embodiment of the present invention, as shown in FIG. 10($e$), skin map 1050 includes a matrix or data group having a plurality of elements, each corresponding to a pixel in any of the white-light or UV images of subject 101. Those matrix elements corresponding to skin pixels in the last white-light image (shown as white blocks in FIG. 10($e$)) are defined as skin elements, and each is assigned a first value.

In contrast, those matrix elements corresponding to non-skin pixels in the last white-light image (shown as black blocks in FIG. 10($e$)) are defined as non-skin elements, and each is assigned a second value that is distinct from the first value. In one exemplary embodiment, the first value is a large number, such as 255, and the second value is a small number, such as 0. Thus, whether a pixel in any of the white-light and UV images is a skin pixel can be easily determined by looking up the value contained in the corresponding element in skin map 1050, and this can be done in step 850.

Figure 11:
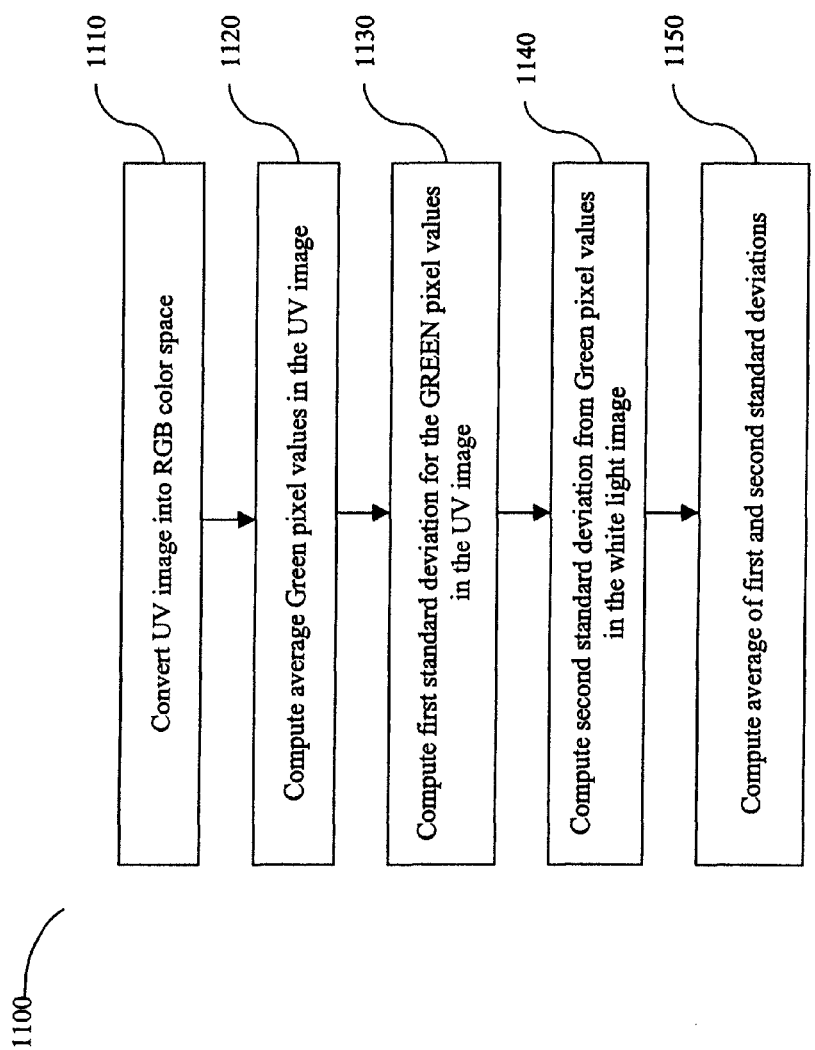
FIG. 11 is a flowchart illustrating process steps for obtaining UV damage results from the digital images according to an exemplary embodiment of the present invention.

In one exemplary embodiment of the present invention, module 730 includes sub-module 1100 for obtaining UV damage results using the skin pixels in at least the first UV image, as illustrated in FIG. 11. Sub-module 1100 includes step 1110 in which the first UV image, if it is not in the RGB color space, is converted into the RGB color space, step 1120 in which an average is computed from all of the green channel values in the skin pixels of the first UV image, and step 1130 in which a first standard deviation is computed from the green channel values in the skin pixels. The first standard deviation value can be used to indicate quantitatively the amount of UV damage in the skin of subject 101.

Alternatively or additionally, sub-module 1100 may include a further step 1140 in which a second standard deviation is computed from the green channel values in the skin pixels of one of the white-light images, and an average of the first and second standard deviation values can be used to indicate quantitatively the amount of UV damage in the skin of subject 101.

In order to visually display the UV damage results in an enhanced view, a UV damage enhanced white-light image is formed in step 1150 that has a plurality of pixels each corresponding to a respective pixel in the first white-light image. Thus, a non-skin pixel in the first white-light image corresponds to a non-skin pixel in the UV damage enhanced white-light image. In one exemplary embodiment, the non-skin pixels in the UV damage enhanced white-light image have the same pixel values as the pixel values in the non-skin pixels in the first white-light image.

For each skin-pixel in the UV damage enhanced white-light image, the red channel and blue channel values therein are the same as those in the corresponding skin pixel in the first white-light image. The green channel value therein is derived from both the green channel value in the corresponding skin pixel in the first white-light image and the green channel value in the corresponding pixel in the first or second UV image.

For example, assuming GEN is the green channel value in a skin pixel in the UV damage enhanced white-light image, and GWL and GUV are the green channel value in the corresponding skin pixels in the first white-light and the first (or second) UV images, respectively, GEN may be assigned to be an average of GWL and GUV, that is:

$$GEN = \frac{1}{2}(GWL + GUV) \quad (1)$$

Other ways of enhancing the UV damage results are also possible, for example:

$$GEN = GWL + (GUV - GAVG) \quad (2)$$

where GAVG is the average green channel value computed in step 1120.

Figure 12:
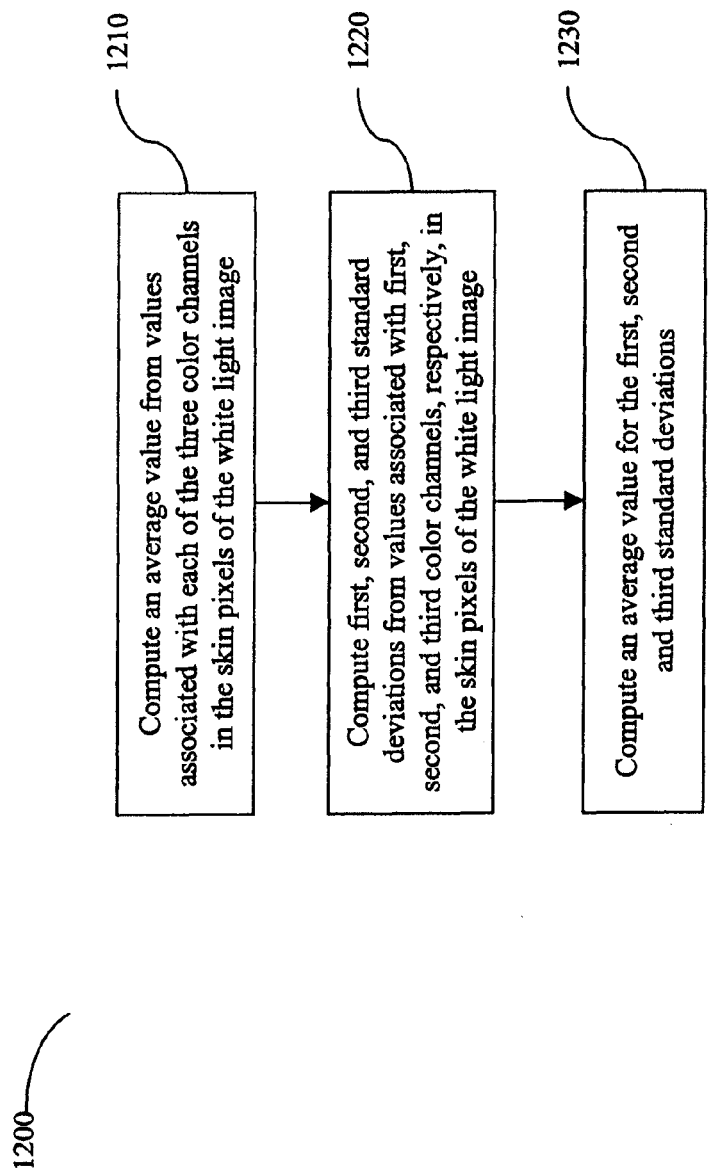
FIG. 12 is a flowchart illustrating process steps for obtaining skin tone results from the digital images according to an exemplary embodiment of the present invention.

In one exemplary embodiment of the present invention, module 730 includes sub-module 1200 for obtaining skin tone results using the skin pixels in any of the white-light images, as illustrated in FIG. 12. Sub-module 1200 includes step 1210 in which an average is computed from values associated with each of the three color channels in the skin pixels of the white-light image, step 1220 in which a standard deviation is computed for each of the color channels in the skin pixels, and step 1230 in which an average of the standard deviation values computed in step 1220 is obtained as a measure of the skin tone of subject 101.

Figure 13A:
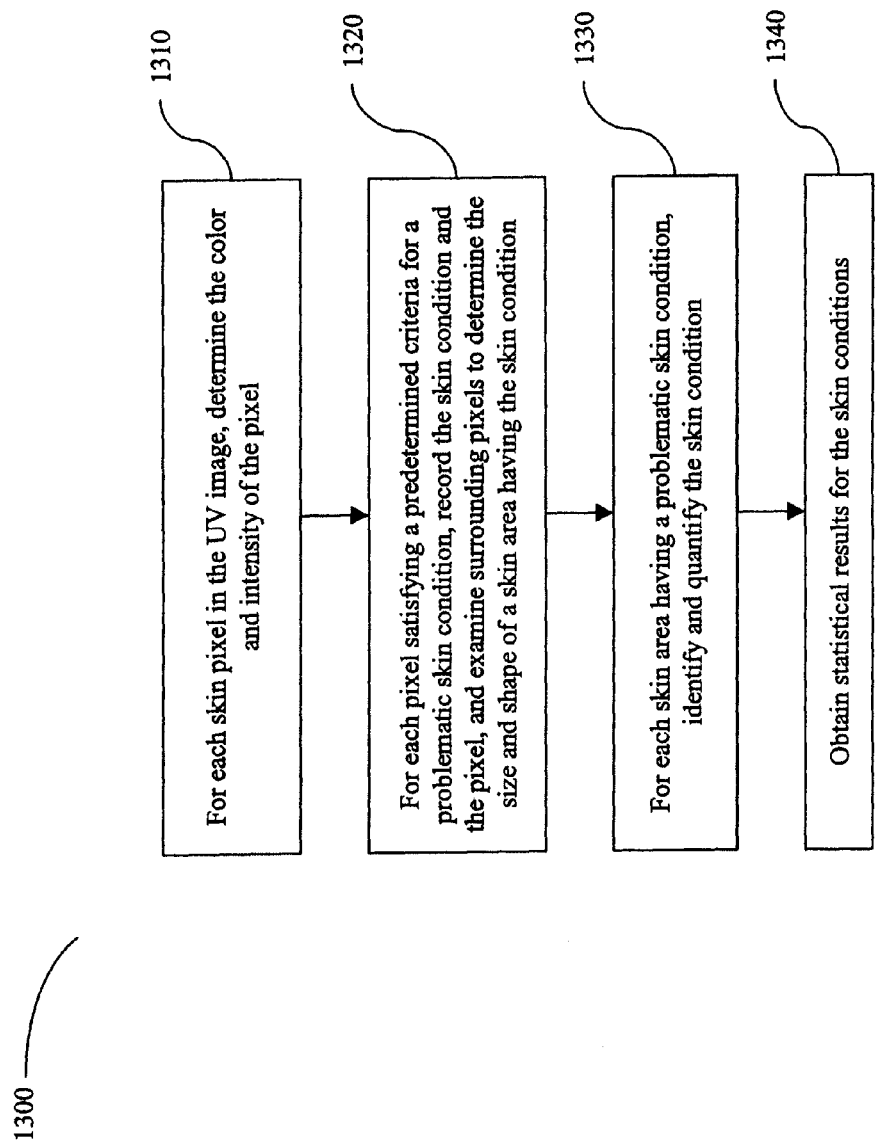
FIG. 13A is a flowchart illustrating process steps for obtaining results related to certain skin conditions according to an exemplary embodiment of the present invention.

In one exemplary embodiment of the present invention, module 730 includes sub-module 1300 for obtaining results related to certain skin conditions, as illustrated in FIG. 13A. Sub-module 1300 includes step 1310 in which color and intensity values are computed from the pixel values associated with each pixel in one of the UV images, and step 1320 in which the color and intensity values for each pixel are examined with reference to at least one look-up table to determine if the pixel satisfies criteria for any of a list of skin conditions in the look-up table. The at least one look-up table may include those compiled using knowledge known in the art, or through proprietary research and/or empirical studies.

For each skin pixel identified to be associated with a certain skin condition, the surrounding pixels are also examined to determine the size and shape of a skin area having the skin condition. In the case of melanoma, the shape and size of an affected skin area can be used to help determine the type and amount of skin cancer damage.

FIG. 13B illustrates an exemplary look-up table for pores and sluggish oil flow that may be included in the at least one look-up table. For example, if a first skin pixel has a white color and an intensity value exceeds 130, the skin pixel is likely one of a group of contiguous pixels that have captured fluorescence coming from an inflamed pore upon illumination by a UV flash. To confirm, surrounding skin pixels are also examined to see if some of them are also white in color and have intensity values over 130. If none or few of the pixels satisfy this criteria, the first skin pixel is not associated with an inflamed pore. Otherwise, an inflamed pore is identified, and in step 1330, the number of skin pixels associated with the inflamed pore is determined as a measure for the shape and size of the pore, and an average of the intensity value associated with the number of skin pixels is computed as a quantitative indication of the severity of the pore.

It should be understood by one of ordinary skill in the art that FIG. 13B only illustrates some examples of the criteria that can be used by module 1300. Alternatively or additionally, module 1300 may use other look-up tables associated with other skin conditions, such as those known in the art. As described hereinabove, skin conditions that may be analyzed by the methods and systems of the present invention may include, but are not limited to, skin tone, UV damage, pores, wrinkles, hydration levels, collagen content, skin type, topical inflammation or recent ablation, keratosis, deeper inflammation, sun spots, different kinds of pigmentation including freckles, moles, growths, scars, acne, fungi, erythema and other artifacts. Information in the skin pixels may also be used to perform feature measurements such as the size and volume of a lip, nose, eyes, ears, chins, cheeks, forehead, eyebrows, among other features.

Sub-module 1300 further includes step 1340 in which statistical results such as a total number of all types skin conditions, and/or a total number of each of a plurality of skin conditions are computed.

Figure 14:
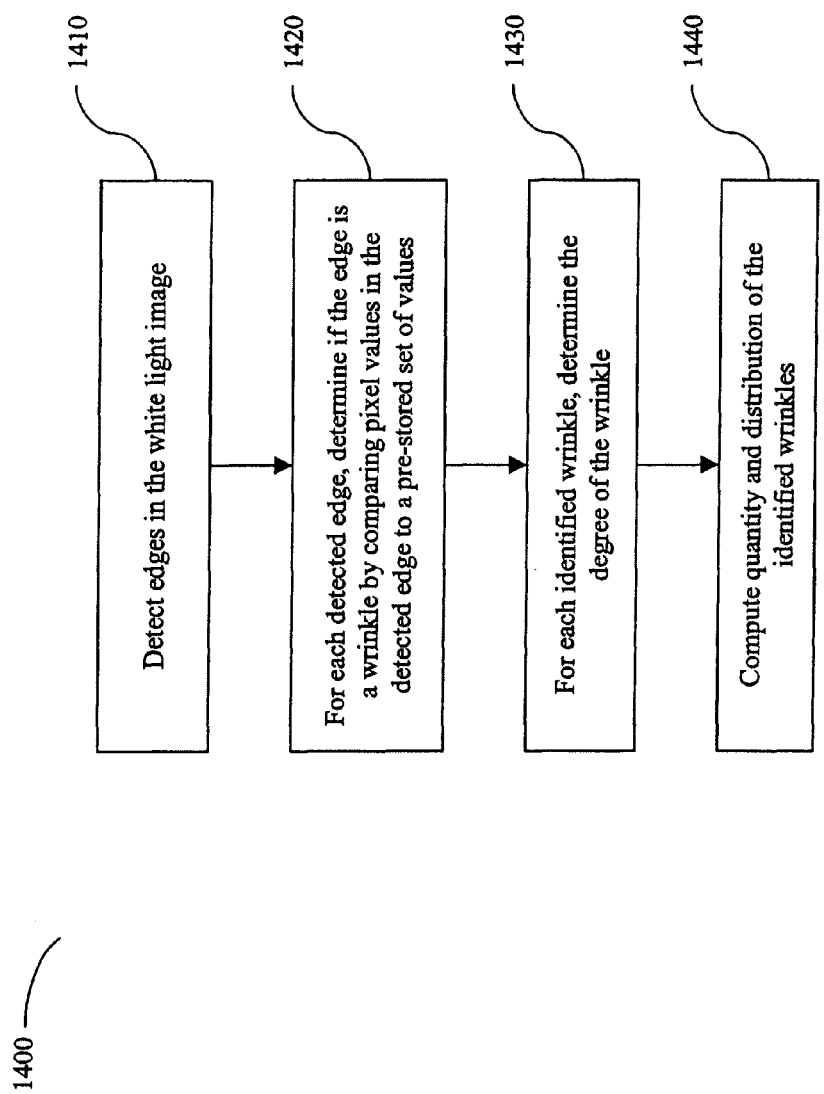
FIG. 14 is a flowchart illustrating process steps for obtaining results related to wrinkles according to an exemplary embodiment of the present invention.

In one exemplary embodiment of the present invention, module 730 further includes sub-module 1400 for evaluating wrinkles on subject 101, as shown in FIG. 14. Sub-module 1400 includes step 1410 in which a conventional or proprietary edge detector, such as the publicly available Canny edge detector, is used to detect edges in any of the white-light image after the non-skin pixels are extracted from the white-light image, and step 1420 in which each detected edge is examined to determine if it is a wrinkle.

In one exemplary embodiment, an edge is determined to be a wrinkle if a predetermined percentage of corresponding pixels have pixel value that satisfy predetermined criteria. In one exemplary embodiment, the predetermined criteria may be derived from pre-stored or recently computed skin color values for subject 101. For example, average values for the red, green, and blue color channels for subject 101 can be used to set the criteria, and if a predetermined percentage, such as over 70% of the pixels corresponding to the edge have their red, green, and blue channel values roughly proportional to the average red, green blue channel values, the edge would be determined as a wrinkle.

Sub-module 1400 may further include step 1430 in which the pixels around the edges are examined to determine the degree of the wrinkle. For example, for a fine line wrinkle, the pixels corresponding to the edge indicating the likely presence of the wrinkle should have intensity values substantially less than those of the surrounding pixels, and for a deep wrinkle, a wider edge should be expected, and there should be a wider line of pixels having depressed intensity values.

Sub-module 1400 may further include step 1440 in which the number of all wrinkles or wrinkles of a certain degree is counted, and a distribution of the wrinkles across the subject may also be computed.

Figure 15A:
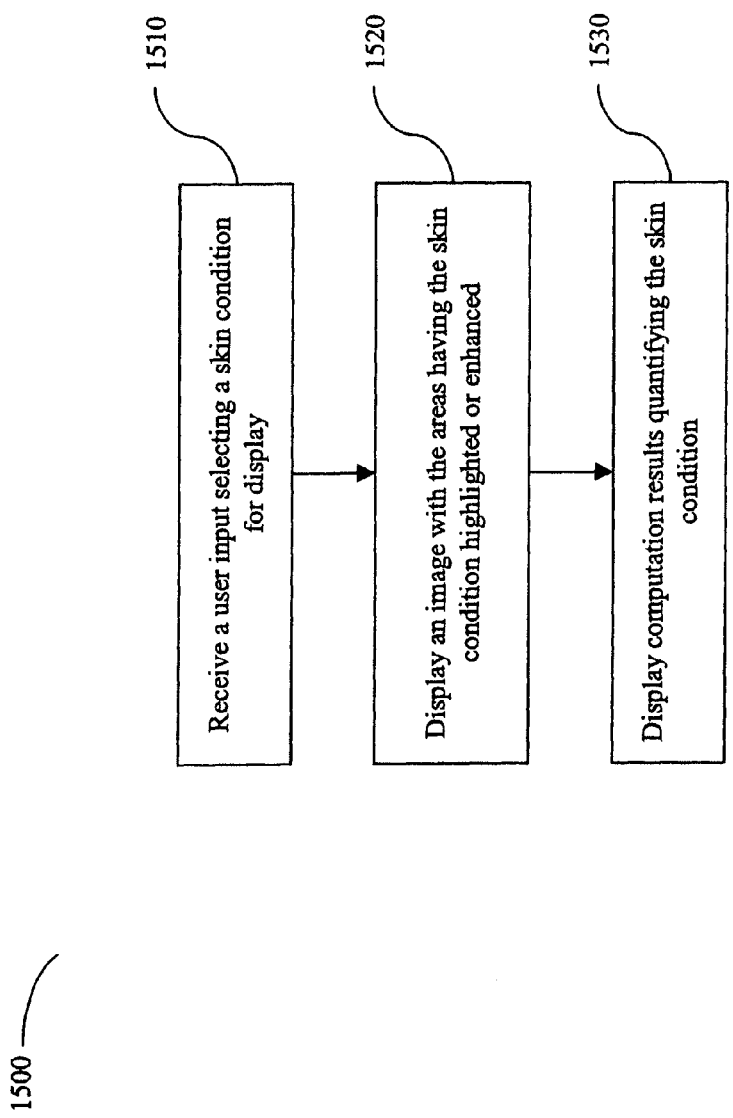
FIG. 15A is a flowchart illustrating process steps for displaying results of skin conditions according to an exemplary embodiment of the present invention.

In one exemplary embodiment, the module for outputting/displaying the results of skin analysis includes sub-module 1500 for displaying the results with a GUI. As shown in FIG. 15A, sub-module 1500 includes step 1510 in which a user input selecting a skin condition for display is received through the GUI, step 1520 in which an image having the selected skin condition highlighted or enhanced is displayed, and step 1530 in which computation results quantifying the skin condition is displayed.

For example, assuming that the user has selected pores or a type of pores as the skin conditions for display, the GUI according to sub-module 1500 may display a color image of the subject with all pores or the selected type of pores highlighted as, for example, bright white dots on the color image. Different pores may also be highlighted using different colors. At the same time or on the same screen, a pore count for all of the pores found, and/or for each of different types of pores may be listed.

Figure 15B:
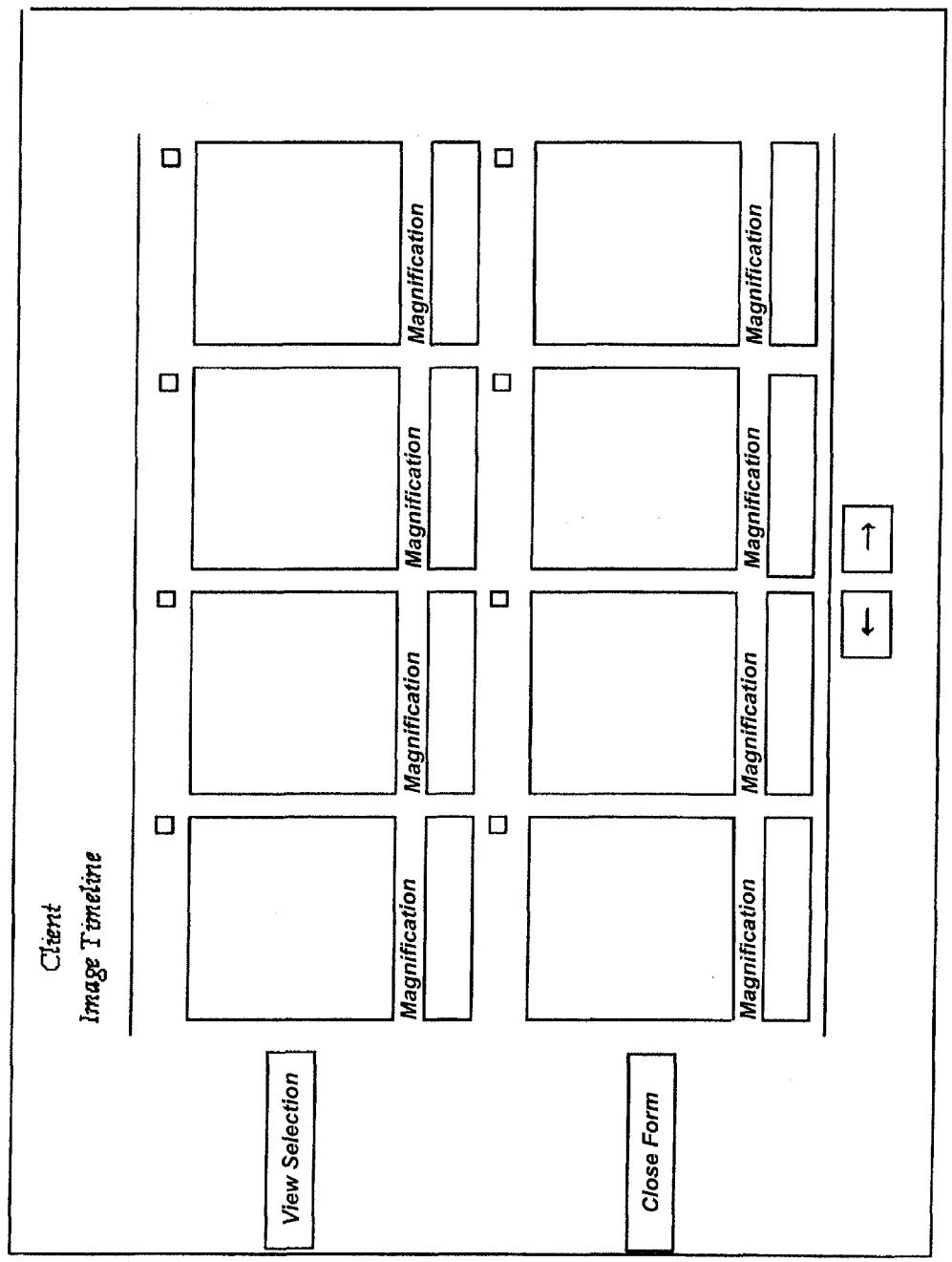
FIG. 15B is a line drawing of a user interface for displaying a timeline of results of skin conditions according to an exemplary embodiment of the present invention.
Figure 15C:
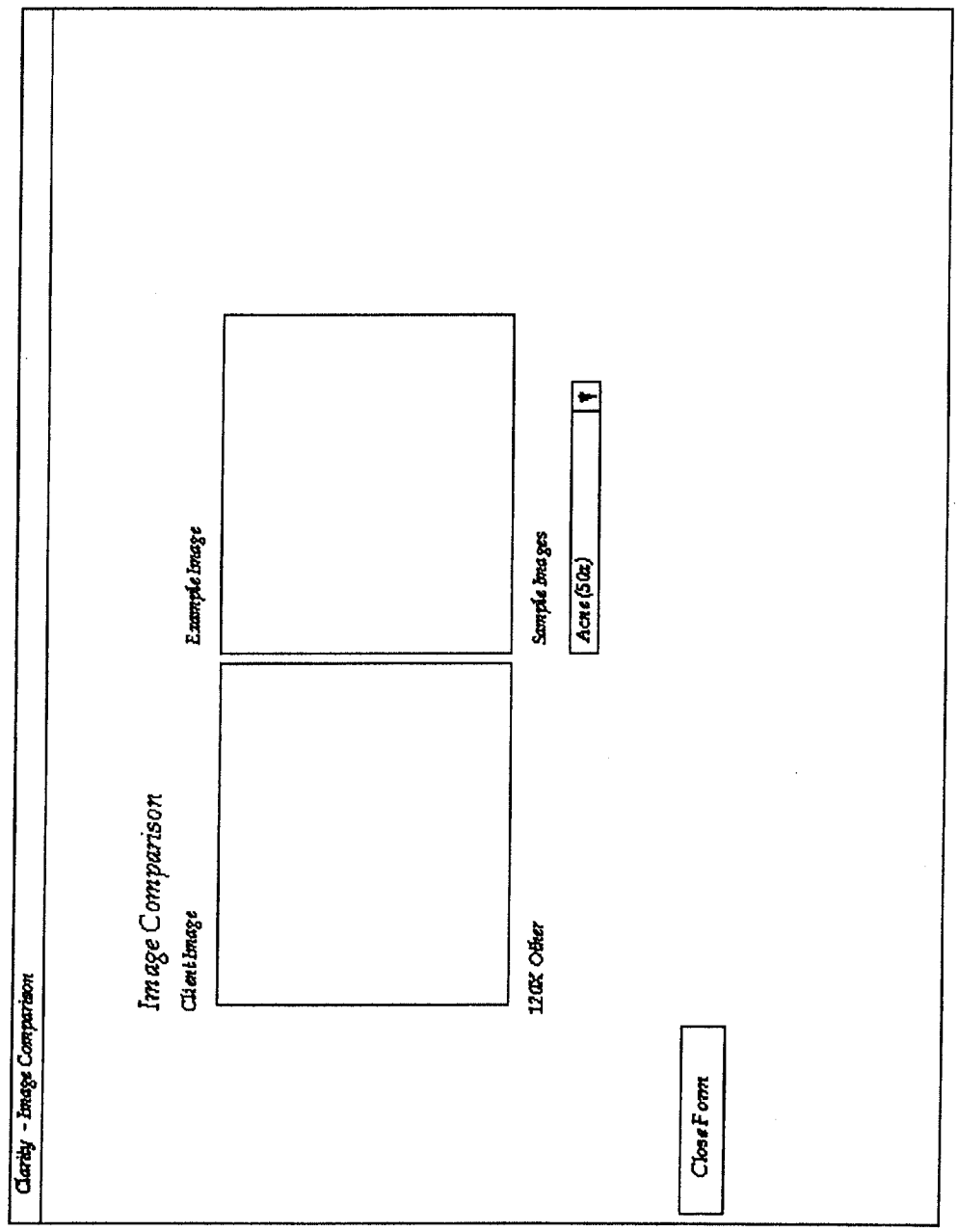
FIG. 15C is a line drawing of a user interface for displaying results related to a selected skin condition as compared with previous results related to the same skin condition.

As shown in FIG. 15B, sub-module 1500 may also display the skin analysis results in a timeline showing changes of selected skin analysis results over time for the same subject 101. As shown in FIG. 15C, sub-module 1500 may also display selected skin analysis results as compared with previous results related to the same skin condition for the same subject 101. The results compared may include statistical results or other data analysis quantifying the skin conditions that are identified and classified for the subject.

The foregoing descriptions of specific embodiments and best mode of the present invention have been presented for purposes of illustration and description only. They are not intended to be exhaustive or to limit the invention to the precise forms disclosed. Specific features of the invention are shown in some drawings and not in others, for purposes of convenience only, and any feature may be combined with other features in accordance with the invention. Steps of the described processes may be reordered or combined, and other steps may be included. The embodiments were chosen and described in order to best explain the principles of the invention and its practical application, to thereby enable others skilled in the art to best utilize the invention and various embodiments with various modifications as are suited to the particular use contemplated. Further variations of the invention will be apparent to one skilled in the art in light of this disclosure and such variations are intended to fall within the scope of the appended claims and their equivalents. The publications referenced above are incorporated herein by reference in their entireties.

What is claimed is:

1. A method for analyzing skin conditions associated with a subject, performed on a system having a portable image acquisition device, a processor and a memory storing one or more programs for execution by the processor to perform the method comprising:
    acquiring a first white-light image and a first UV image of at least a portion of a body surface of the subject at the portable image acquisition device, the first white-light and UV images including a plurality of pixels, the pixels in the first white-light image corresponding to respective pixels in the first UV image;
    sending the first white-light image and the first UV image to the processor for analysis; and
    at the processor,
        generating a skin mask having a plurality of elements corresponding to respective pixels in the first white-light image and having been assigned a value;
        analyzing properties of pixels in at least the first white-light image to identify skin pixels in the first white-light and UV images, wherein the step of identifying comprises, for a pixel in the first white-light or UV image, determining if the pixel is a skin pixel by looking up the value in a corresponding element in the skin mask having said assigned values; and
        obtaining results associated with at least one skin condition using information in the skin pixels in at least one of the first white-light and UV images.

2. The method of claim 1, wherein the portable image acquisition device is selected from the group consisting of: a film-based camera; a digital camera; a wireless phone; a personal digital appliance; a desktop computer; a notebook computer; a digital music player; a set-top box; a video game unit; and an entertainment unit.

3. The method of claim 1, wherein the step of acquiring comprises:
    applying UV light to the subject to acquire the first UV image; and
    applying white light to the subject to acquire the first white-light image.

4. The method of claim 3, further comprising placing a light-absorbing cloak to cover part of the subject before acquiring the first UV image.

5. The method of claim 1, further comprising orienting an image sensor to adjust an aspect ratio of the first white-light and UV images.

6. The method of claim 1, wherein generating the skin mask comprises:
    converting the first white-light image into at least one second white-light image of at least one second color space, the pixels in the at least one second white-light image corresponding to respective pixels in the first white-light image and to respective elements in the skin mask; and
    for an element in the skin-mask:
    determining if pixel properties associated with the corresponding pixel in each of the white-light images satisfy predefined criteria for skin pixels associated with a respective color space; and
    assigning one of first and second values to the element.

7. The method of claim 6, wherein the step of assigning one of the first and second values comprises consulting a coordinate reference.

8. The method of claim 1, wherein the at least one skin condition is selected from a group consisting of: skin tone; UV damage; pores; wrinkles; hydration levels; collagen content; skin type; topical inflammation; ablation; keratosis; deeper inflammation; sun spots; pigmentation; moles; growths; scars; acne; fingi; and erythema.

9. The method of claim 8, wherein the step of obtaining comprises using information in the skin pixels of one or both of the first white-light and UV images to obtain UV damage results associated with the subject.

10. The method of claim 9, wherein the information in skin pixels of the first white-light and UV images includes values associated with three color channels, and results associated with UV damage are obtained from values associated with one of the three color channels in the skin pixels of the first UV image.

11. The method of claim 8, wherein a skin pixel of the first white-light image includes values associated with three color channels, and the step of obtaining comprises using values associated with all of the three channels in the skin pixels of the first white-light image to obtain skin tone results that indicate an evenness of skin tone associated with the subject.

12. The method of claim 11, wherein the step of obtaining further comprises computing a standard deviation for each of the three color channels.

13. The method of claim 8, wherein the step of obtaining comprises:
    computing a color value and an intensity value associated with a skin pixel in the first UV image; and
    for a skin pixel in the first UV image, determining if the color and intensity values fall within predetermined ranges for at least one skin condition.

14. The method of claim 13, wherein the step of obtaining further comprises, for skin pixels in the UV image that have color and intensity values falling within predetermined ranges for a specified skin condition, determining a size of a skin area adjacent the skin pixels and having the specified skin condition by examining surrounding skin pixels for the specified skin condition.

15. The method of claim 14, wherein the specified skin condition is related to a specific type of pores, and the step of obtaining further comprises counting skin areas having the specified skin condition to obtain a number of the specific type of pores.

16. The method of claim 15, wherein the at least one skin condition includes a plurality of types of pores, and the step of obtaining further comprises, for skin pixels in the UV image that have color and intensity values falling within predetermined ranges for each of the plurality of types of pores,
   determining a size of a pore by examining surrounding skin pixels to determine if they belong to a same pore; and
   counting the pores to obtain a pore count.

17. The method of claim 13, wherein the at least one skin condition includes at least one type of pores selected from the group consisting of: inflamed pores; bacteriostatic pores; sluggish oil flow; and deeply inflamed pores.

18. The method of claim 1, wherein the step of obtaining comprises measuring features in the subject to quantify their size and volume.

19. The method of claim 1, further comprising displaying results associated with at least one selected skin condition.

20. The method of claim 19, wherein the at least one selected skin condition includes pores, and the step of displaying comprises:
   displaying on a user interface an image of the subject with at least one type of pores highlighted; and
   displaying a pore count value indicating a number of at least one type of pores associated with the subject.

21. The method of claim 20, wherein at least two types of pores are highlighted in the image using different colors, each color corresponding to a respective type of pores.

22. The method of claim 20, wherein the at least one selected skin condition includes UV damage, and the step of displaying comprises displaying an image of the subject with areas having UV damage highlighted.

23. The method of claim 22, wherein pixels in the first white-light and UV images include values associated with first, second and third color channels, and the step of displaying the image of the subject comprises:
   composing an image for display having pixels corresponding to a respective pixel in the first white-light image and to a respective pixel in the first UV image;
   for a pixel in the image for display, assigning first, second, and third values to respective ones of the first, second, and third color channels in the pixel, the first and second values being proportional to respective ones of the values associated with the first and second color channels in the corresponding pixel of the first white-light image, and the third value being proportional to an average of the values associated with the third color channel in corresponding pixels of the first white-light and UV images.

24. The method of claim 19, wherein the step of displaying comprises displaying both current and prior results associated with at least one selected skin condition for the subject for comparison.

25. The method of claim 24, wherein displaying both current and prior results comprises aligning images obtained for generating the previous results with images obtained for generating the current results.

26. A method for analyzing skin conditions associated with a subject, performed on a system having a portable image acquisition device, a processor and a memory storing one or more programs for execution by the processor to perform the method comprising:
   acquiring a first white-light image and a first UV image of at least a portion of a body surface of the subject at the portable image acquisition device, the first white-light and UV images including a plurality of pixels, the pixels in the first white-light image corresponding to respective pixels in the first UV image;
   sending the first white-light image and the first UV image to the processor for analysis; and
   at the processor,
      analyzing properties of pixels in at least the first white-light image to identify skin pixels in the first white-light and UV images, wherein the first white-light image is of a first color space and wherein the step of identifying comprises:
         for a pixel in the first white-light image,
            determining if pixel values associated therewith satisfy a first set of predefined criteria for skin pixels;
         converting the first white-light image into at least one second white-light image of at least one second color space; and
         for at least one second white-light image,
            determining if pixel values associated with a pixel in the at least one second white-light image satisfy a respective set of predefined criteria for skin pixels; and
   obtaining results associated with at least one skin condition using information in the skin pixels in at least one of the first white-light and UV images.

27. The method of claim 26, wherein the step of identifying further comprises consulting a coordinate reference.

* * * * *